US009068621B1

(12) United States Patent
Halladay et al.

(10) Patent No.: US 9,068,621 B1
(45) Date of Patent: Jun. 30, 2015

(54) ROTARY WING AIRCRAFT BEARING FOR ROTARY WING AIRCRAFT MOTIONS

(75) Inventors: James R. Halladay, Erie, PA (US); Patrick M. Sheridan, North East, PA (US); Marshall W. Downing, Fairview, PA (US); Zachary Fuhrer, Erie, PA (US)

(73) Assignee: LORD Corporation, Cary, NC (US)

( * ) Notice: Subject to any disclaimer, the term of this patent is extended or adjusted under 35 U.S.C. 154(b) by 1197 days.

(21) Appl. No.: 12/927,754

(22) Filed: Nov. 23, 2010

(51) Int. Cl.
*F16F 7/00* (2006.01)
*F16F 1/40* (2006.01)
(Continued)

(52) U.S. Cl.
CPC ................. *F16F 1/40* (2013.01); *F16F 1/3605* (2013.01); *F16C 41/008* (2013.01)

(58) Field of Classification Search
CPC ........... F16F 1/406; F16F 1/3842; F16F 1/40; F16F 1/403; F16F 1/3605; F16C 33/04; F16C 41/008; F16C 27/063; F16C 11/0609
USPC ......... 267/141.1, 140.2, 140.4, 294; 384/221, 384/222; 416/134 A, 134 R, 140; 464/69, 464/70, 71, 72, 90
See application file for complete search history.

(56) References Cited

U.S. PATENT DOCUMENTS

| 3,134,445 A | 5/1964 | Hotchkiss |
| 3,258,805 A | 7/1966 | Rossnan |

(Continued)

FOREIGN PATENT DOCUMENTS

| WO | 79/00033 A1 | 1/1979 |
| WO | 00/17047 A1 | 3/2000 |

OTHER PUBLICATIONS

Randolph Research, LamiFlex TM Hi-Load Rubber Laminate Bearings/Seals, www.randolphresearch.com, Nov. 10, 2009, 2 pages.
(Continued)

*Primary Examiner* — Pamela Rodriguez

(57) ABSTRACT

A rotary wing aircraft bearing that provides a constrained relative motion between a first rotary wing aircraft member and a second rotary wing aircraft member. The bearing includes an elastomeric mold bonded laminated bearing stack, the elastomeric mold bonded laminated bearing stack including a plurality of mold bonded alternating layers of nonelastomeric shim member layers and elastomeric shim members layers, the alternating layers having an exterior surface and an interior center distal from the exterior surface. At least one of the elastomeric shim members layers has an interior elastomer region distal from the exterior surface, the interior elastomer region formed an interior cured elastomer composition having at least a first interior optical characteristic ingredient, and an exterior elastomer region encompassing the interior elastomer region, the exterior elastomer region proximate the exterior surface, the exterior elastomer region formed from an exterior cured elastomer composition having at least a second exterior optical characteristic ingredient, the at least second exterior optical characteristic ingredient different than the interior cured elastomer composition first interior optical characteristic ingredient, wherein with an elastomer void crack propagating from the exterior surface inward towards the interior elastomer region and a repeated rotary wing aircraft relative motion between the first rotary wing aircraft member and the second rotary wing aircraft member generates a plurality of interior cured elastomer composition crumbs to be expelled from the elastomer void, the interior cured elastomer composition crumbs optically distinguishable from the exterior cured elastomer composition.

48 Claims, 26 Drawing Sheets

(51) Int. Cl.
*F16F 1/36* (2006.01)
*F16C 41/00* (2006.01)

(56) References Cited

U.S. PATENT DOCUMENTS

| | | | |
|---|---|---|---|
| 3,578,055 A | 5/1971 | French et al. | |
| 3,759,631 A | 9/1973 | Rybicki | |
| 3,778,189 A | 12/1973 | Ferris | |
| 3,787,102 A * | 1/1974 | Moran | 384/221 |
| 3,814,160 A | 6/1974 | Creasey | |
| 3,941,433 A | 3/1976 | Dolling et al. | |
| 4,105,266 A | 8/1978 | Finney | |
| 4,142,833 A | 3/1979 | Rybicki et al. | |
| 4,244,677 A | 1/1981 | Noehren et al. | |
| 4,251,187 A | 2/1981 | Hollrock | |
| 4,256,354 A | 3/1981 | Peterson | |
| 4,297,078 A | 10/1981 | Martin | |
| 4,357,057 A | 11/1982 | Peterson et al. | |
| 4,365,936 A | 12/1982 | Hatch | |
| 4,373,862 A | 2/1983 | Ferris et al. | |
| 4,439,106 A | 3/1984 | Ferris et al. | |
| 4,836,029 A | 6/1989 | Skala et al. | |
| 4,927,481 A | 5/1990 | McGregor | |
| 5,186,686 A * | 2/1993 | Staples et al. | 464/69 |
| 5,188,513 A | 2/1993 | Byrnes | |
| 5,213,739 A | 5/1993 | Dickerson et al. | |
| 5,303,756 A | 4/1994 | Hill | |
| 5,399,309 A | 3/1995 | Simmons | |
| 5,817,365 A | 10/1998 | Richardson et al. | |
| 5,894,682 A | 4/1999 | Broz | |
| 6,023,967 A | 2/2000 | Chung et al. | |
| 6,848,886 B2 | 2/2005 | Schmaling et al. | |
| 6,922,916 B1 | 8/2005 | Potter | |
| 7,290,985 B2 | 11/2007 | James et al. | |
| 7,565,778 B2 | 7/2009 | Azeau | |
| 7,896,747 B2 | 3/2011 | Russell | |
| 8,205,560 B2 | 6/2012 | East et al. | |
| 8,632,062 B2 * | 1/2014 | James | 267/141.1 |
| 2004/0208745 A1 | 10/2004 | Schmaling et al. | |
| 2005/0248191 A1 | 11/2005 | Azeau | |
| 2007/0231140 A1 | 10/2007 | James | |
| 2008/0023586 A1 | 1/2008 | Russell | |
| 2010/0199880 A1 | 8/2010 | East et al. | |
| 2013/0121828 A1 * | 5/2013 | Davis et al. | 416/134 A |

OTHER PUBLICATIONS

Randolph Research, LamiFlex TM Bearings for Helicopter Blade Retention, www.randolphresearch.com/helbrg.htm, Nov. 10, 2009, 4 pages.

* cited by examiner

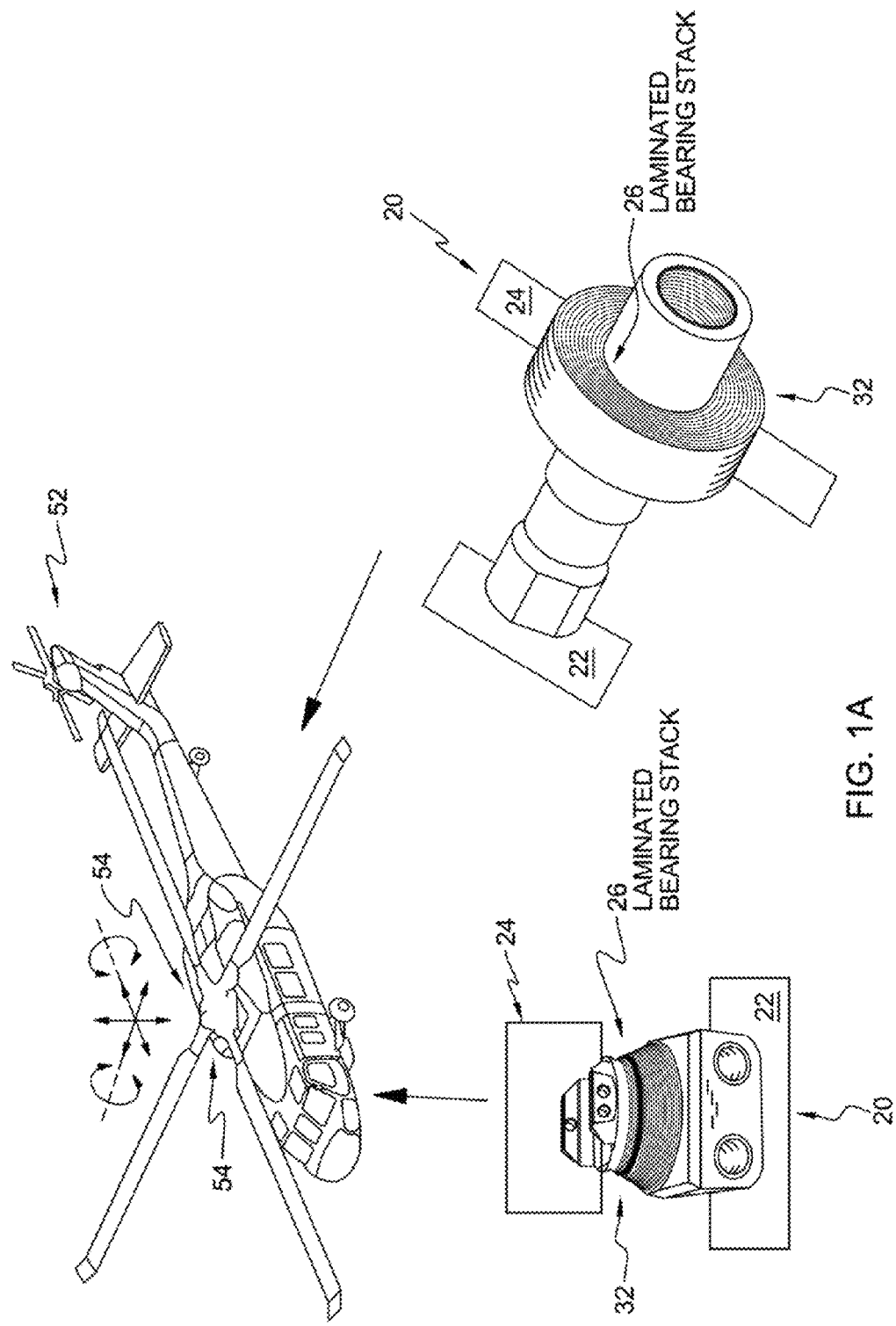

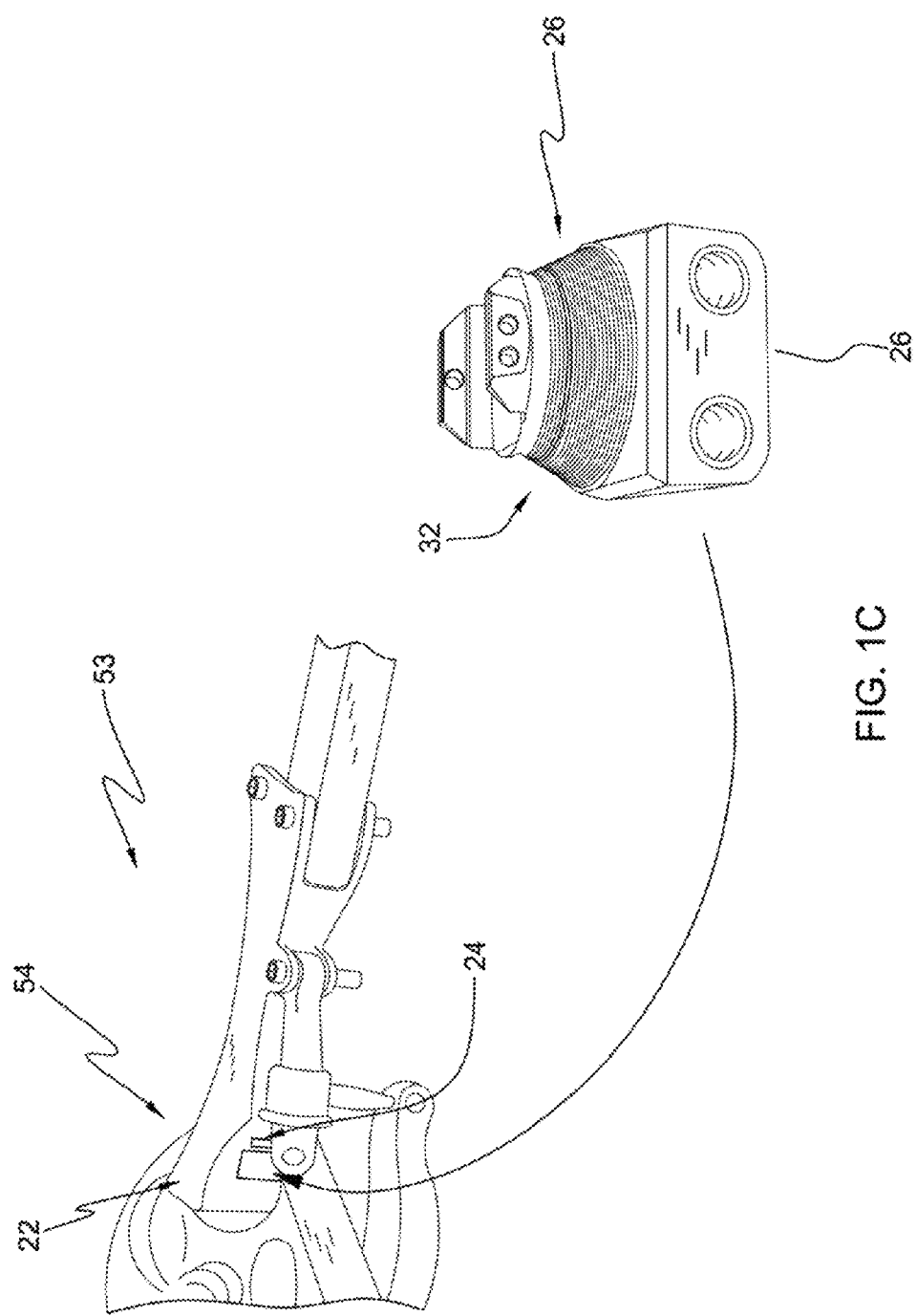

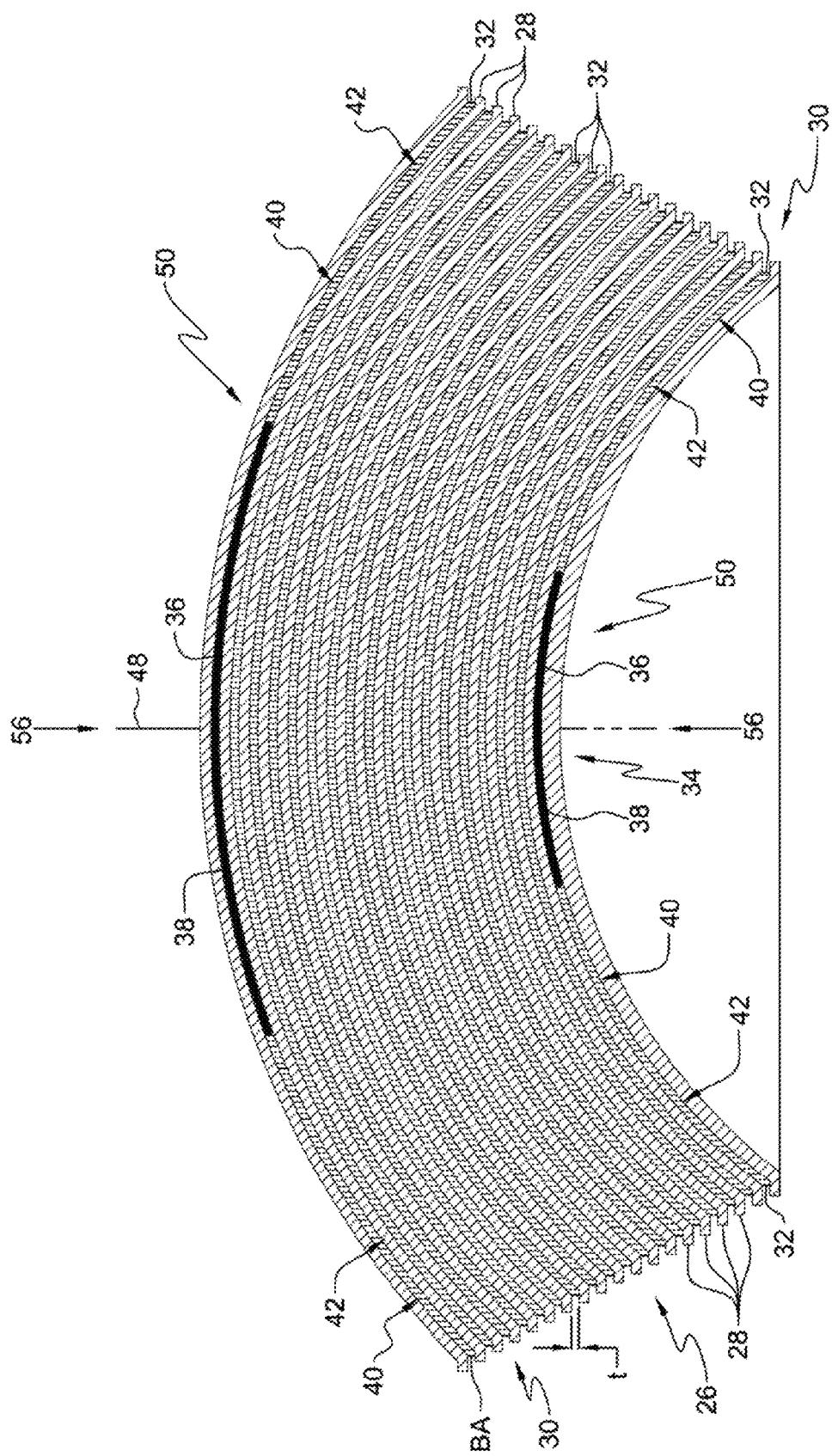

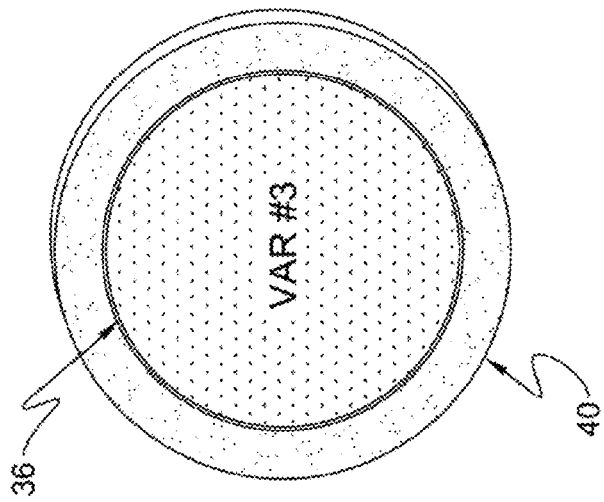
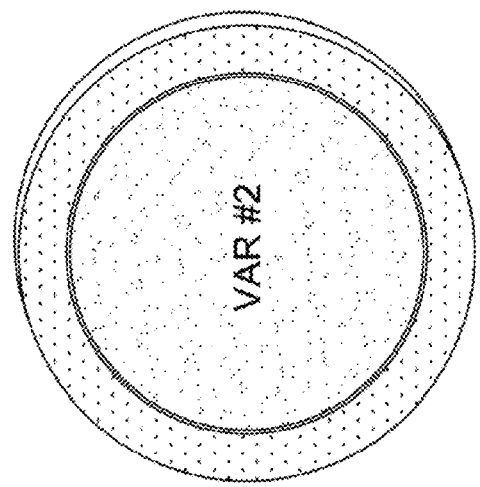
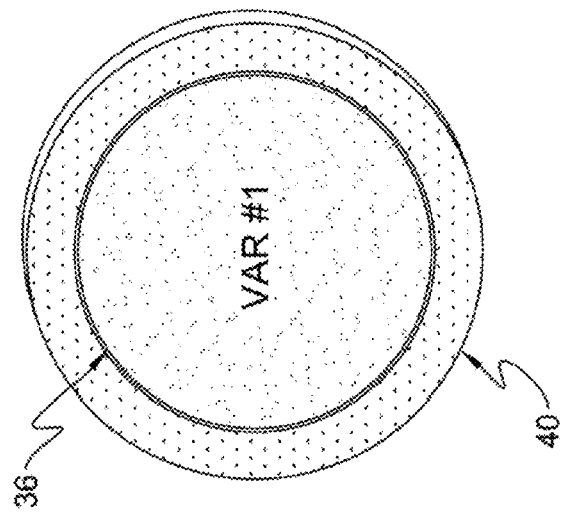
FIG. 3B

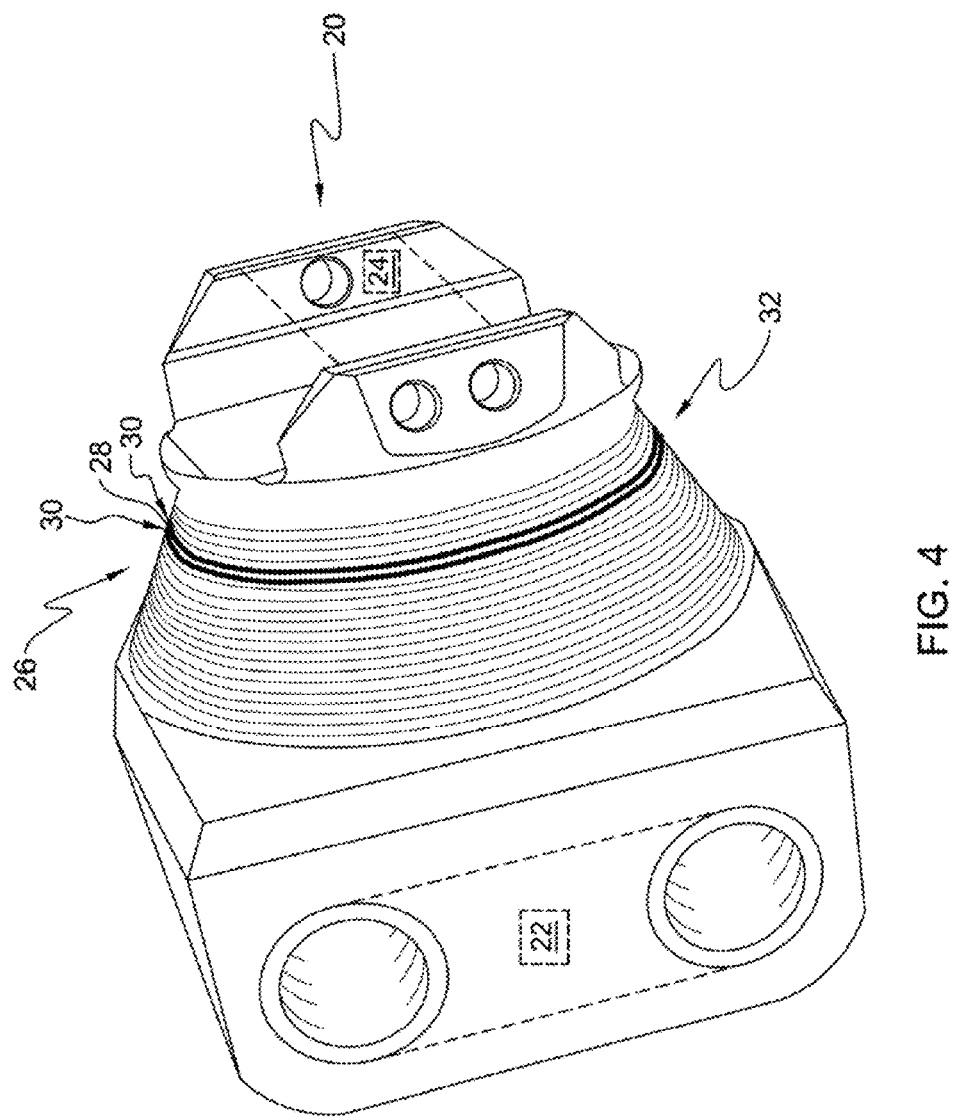

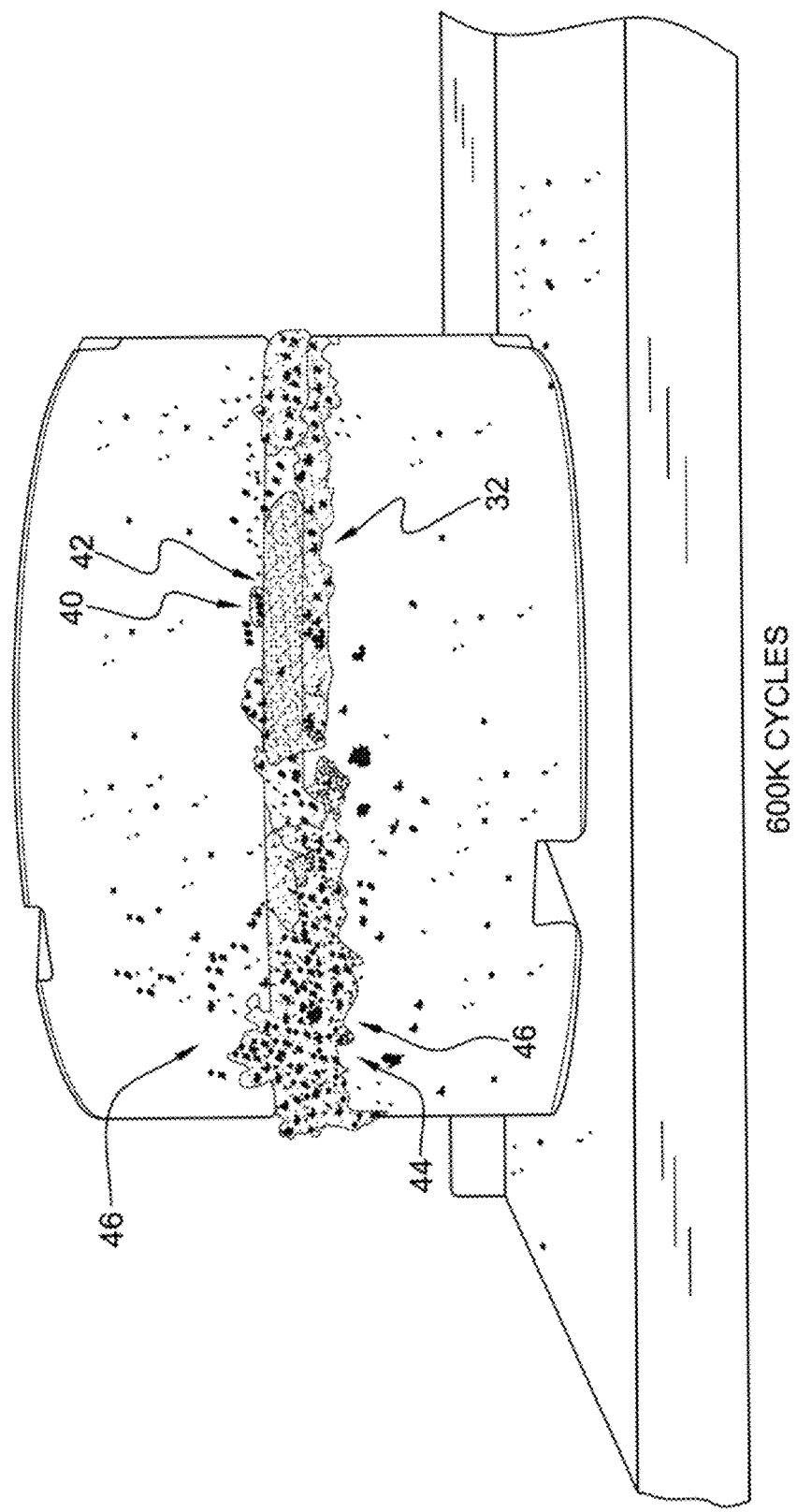

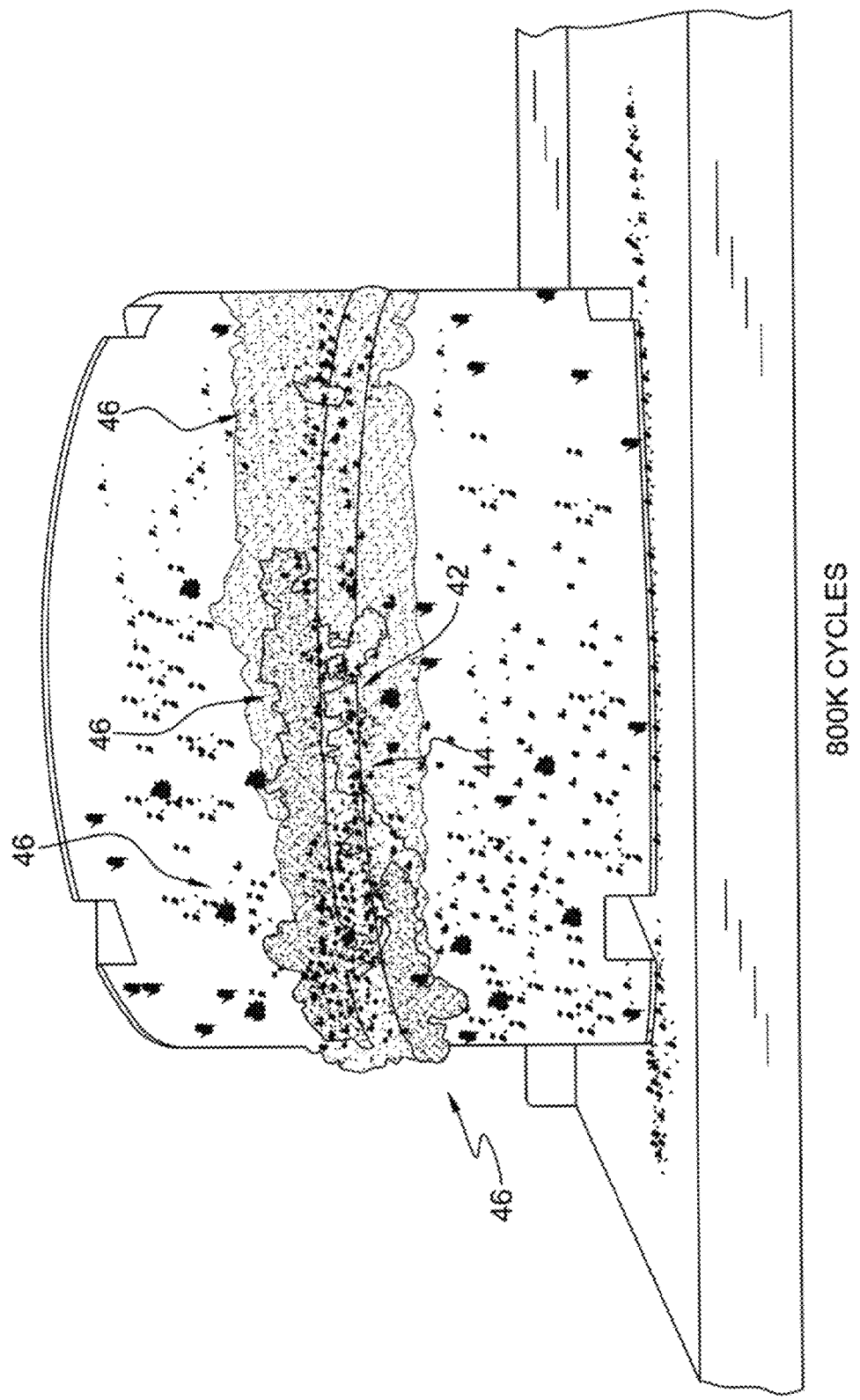

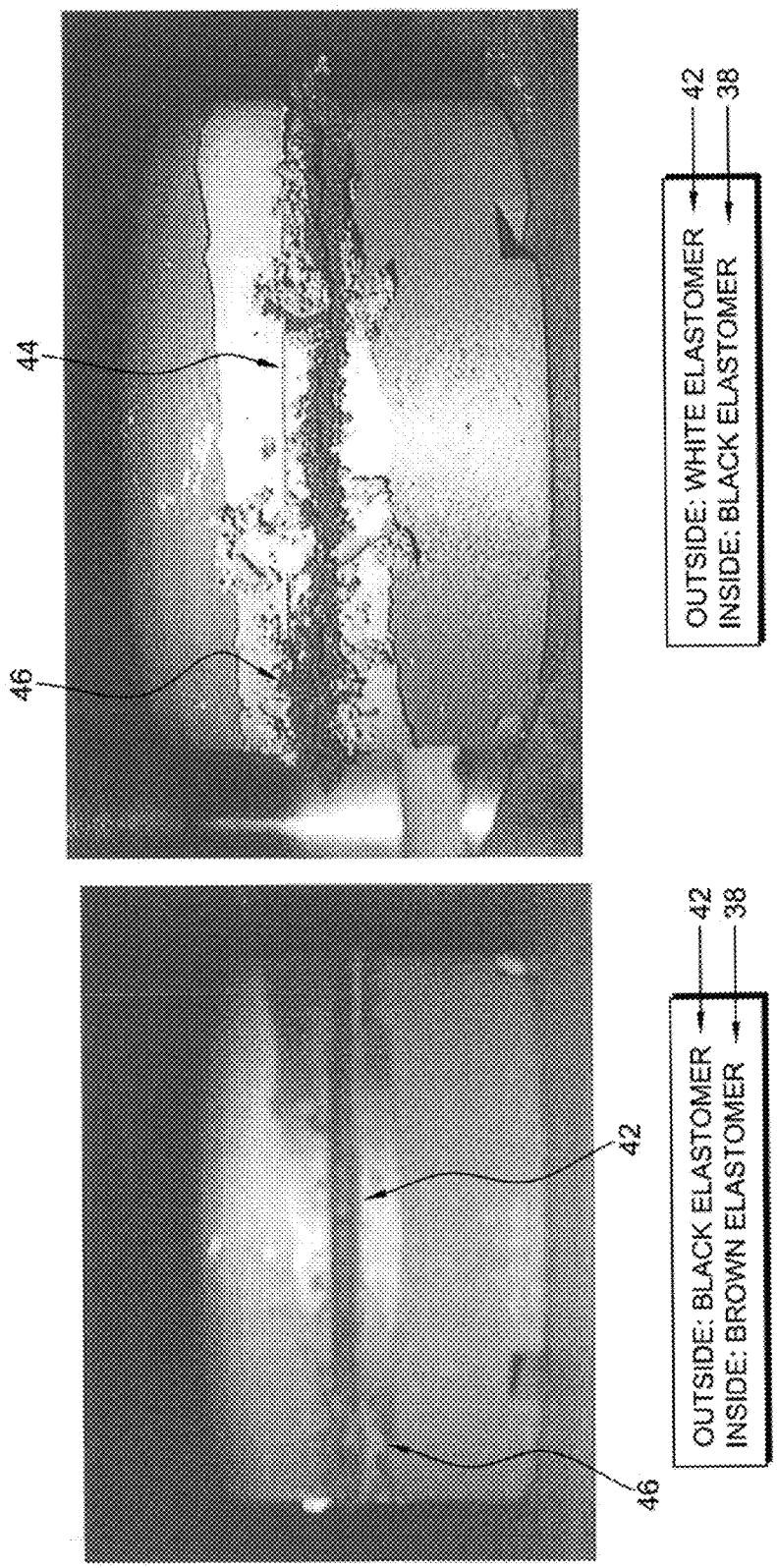

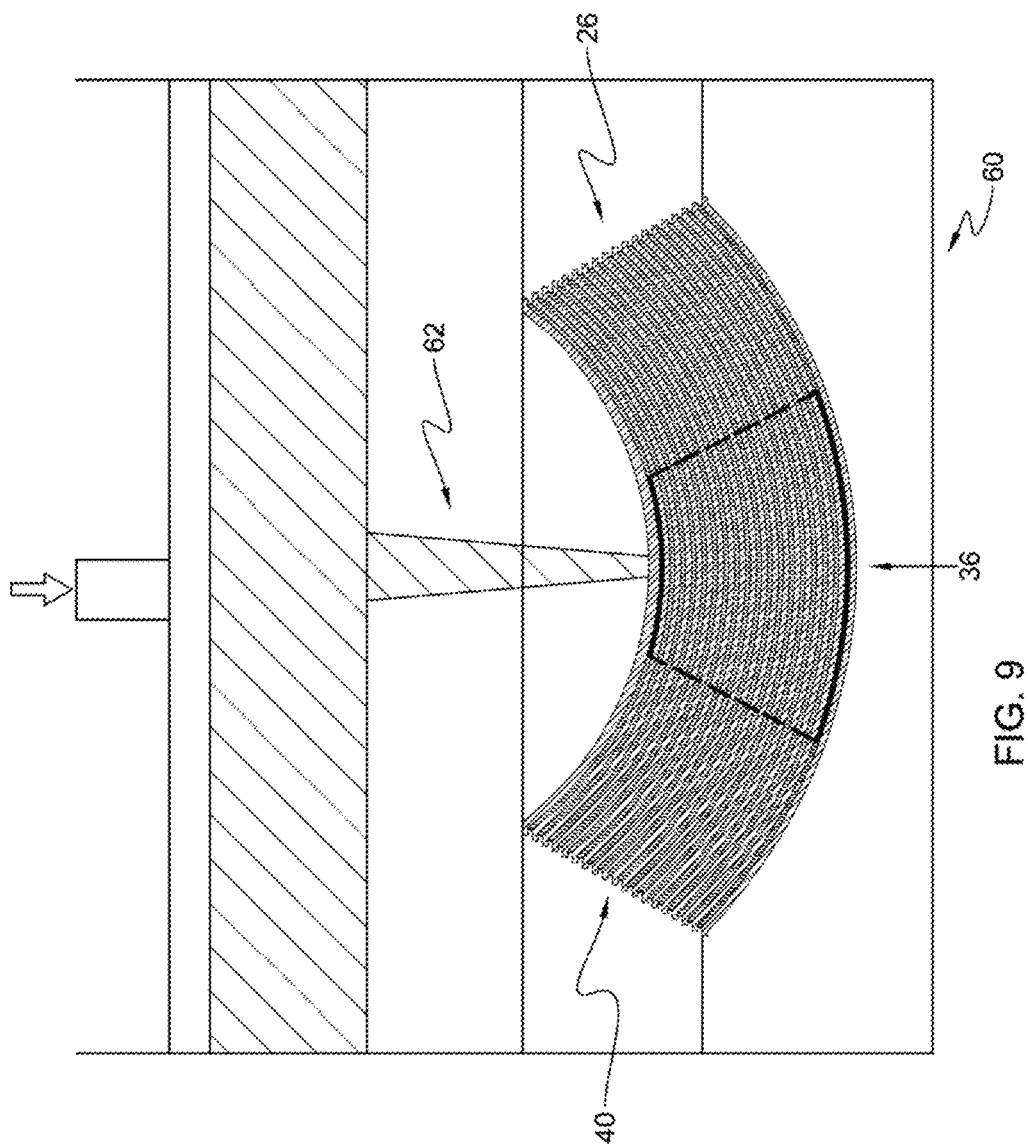

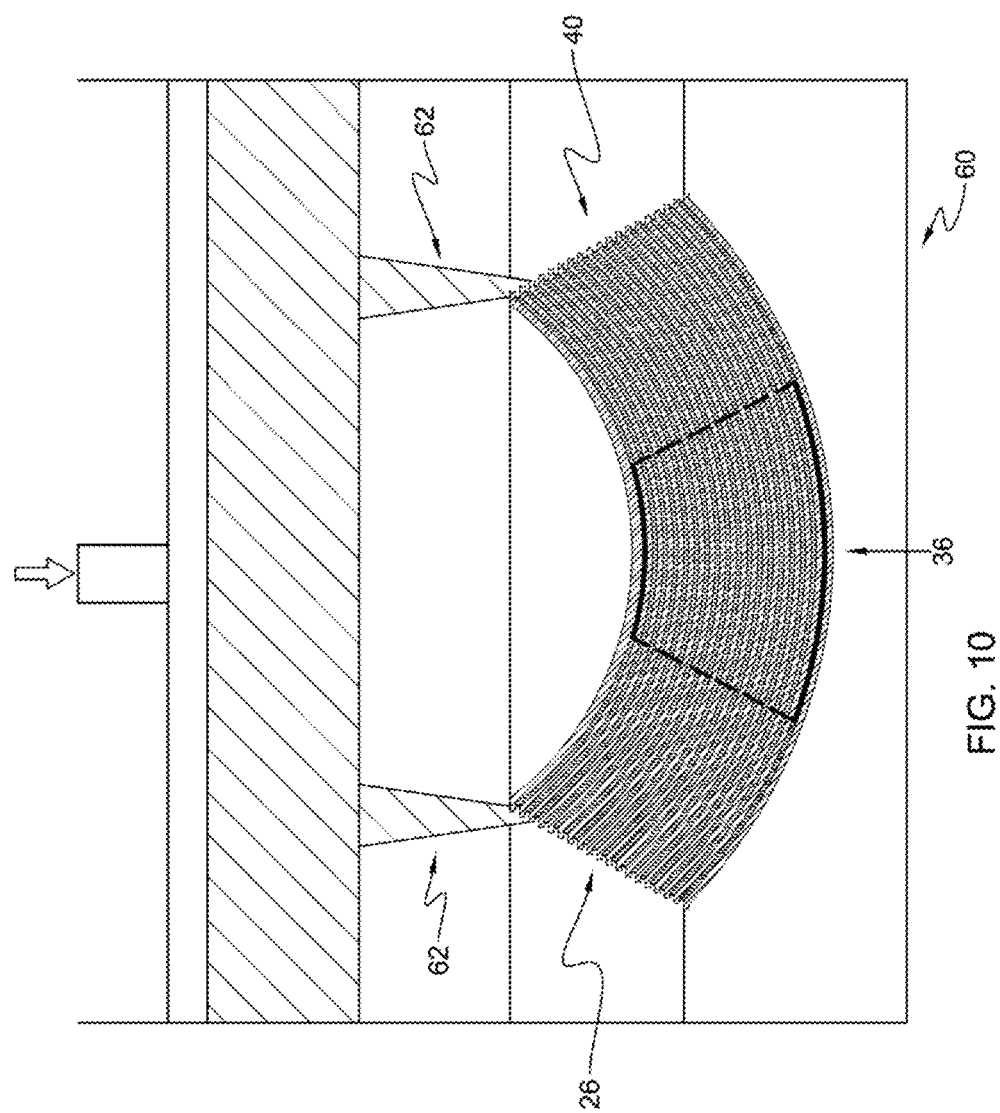

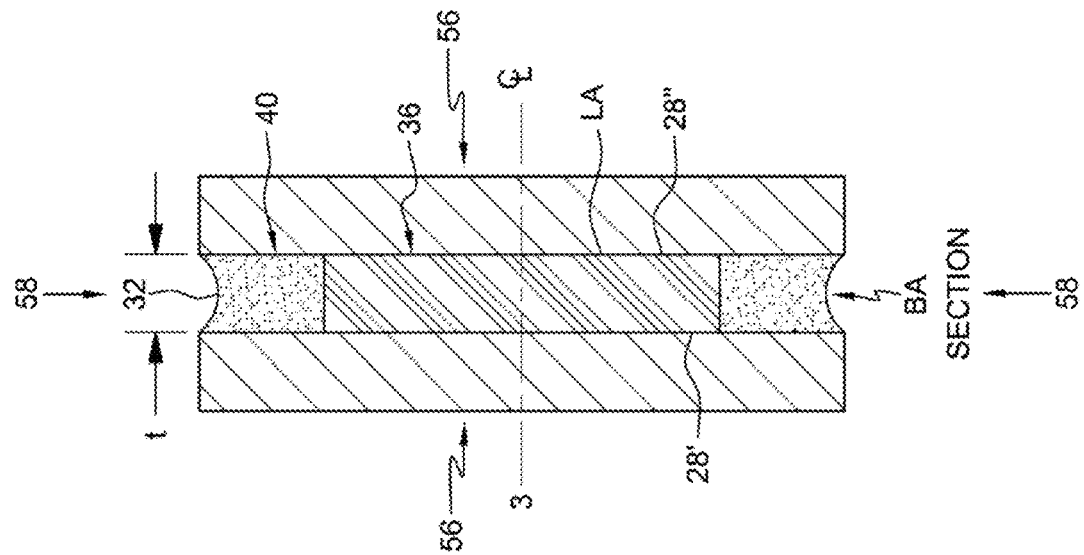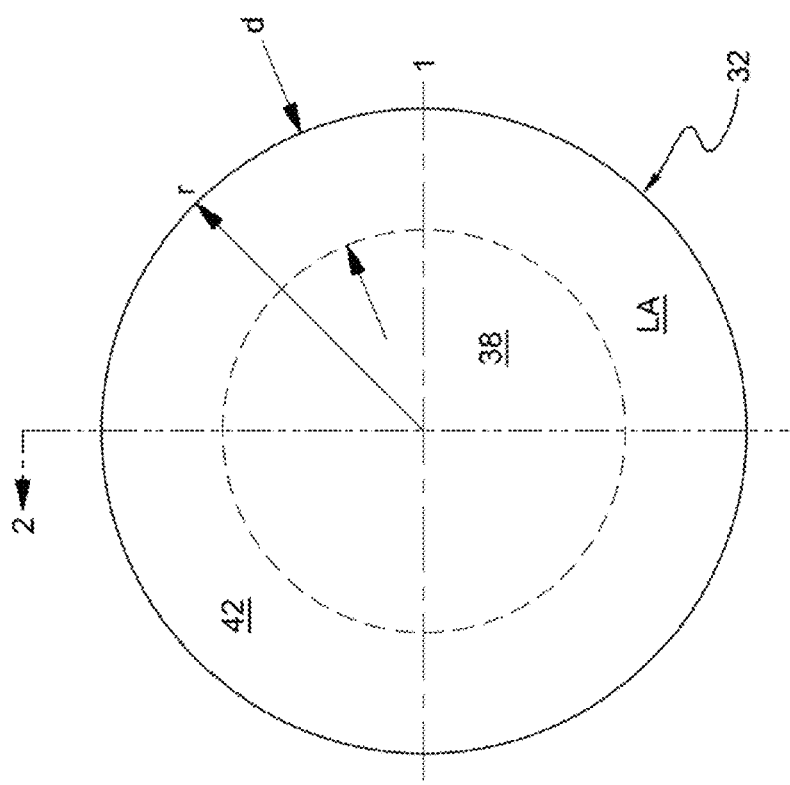
FIG. 16

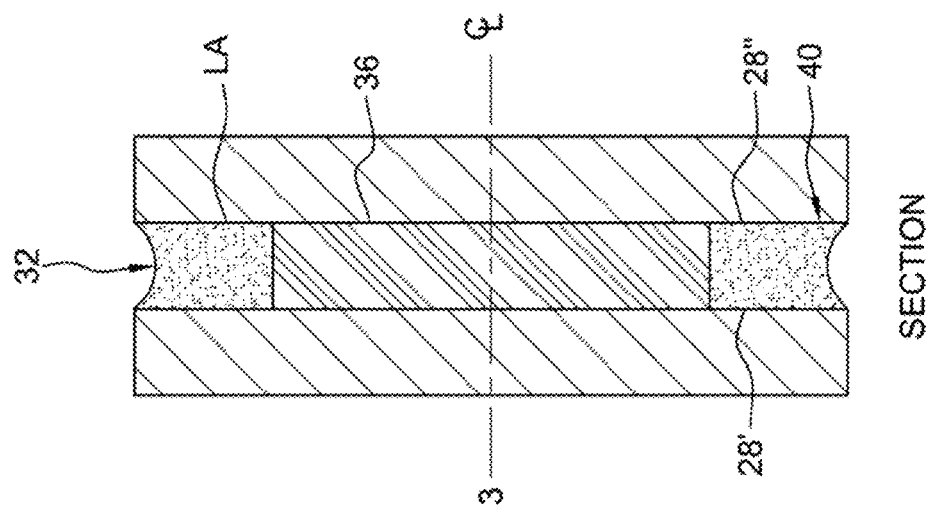
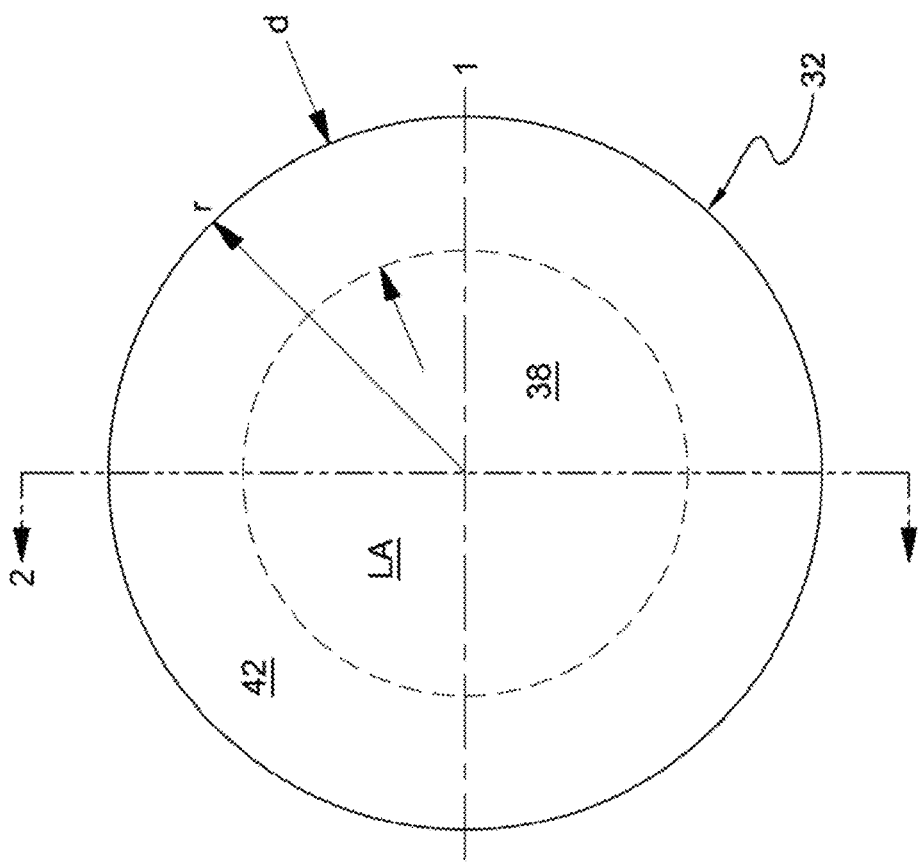
FIG. 17

ROTARY WING AIRCRAFT BEARING FOR ROTARY WING AIRCRAFT MOTIONS

This application claims the benefit of U.S. Provisional Application 61/263,799 filed on Nov. 23, 2009 (A ROTARY WING AIRCRAFT BEARING FOR ROTARY WING AIRCRAFT MOTIONS) which is herein incorporated by reference.

FIELD OF THE INVENTION

The invention relates to the field of rotary wing aircraft such as helicopters. The invention relates to the field of rotary wing aircraft bearings for connecting rotary wing vehicle members and providing relative motion between the connecting rotary wing vehicle members. More particularly the invention relates to the field of elastomeric high capacity laminated bearings for rotary wing aircraft.

SUMMARY OF THE INVENTION

In an embodiment the invention includes a rotary wing aircraft bearing to provide a constrained relative motion between a first rotary wing aircraft member and a second rotary wing aircraft member. The bearing includes an elastomeric mold bonded laminated bearing stack, the elastomeric mold bonded laminated bearing stack including a plurality of mold bonded alternating layers of nonelastomeric shim member layers and elastomeric shim members layers, the alternating layers having an exterior surface and an interior center distal from the exterior surface. At least one of the elastomeric shim members layers comprised of an interior elastomer region distal from the exterior surface, the interior elastomer region comprised of an interior cured elastomer composition having at least a first interior optical characteristic ingredient, and an exterior elastomer region encompassing the interior elastomer region, the exterior elastomer region proximate the exterior surface, the exterior elastomer region comprised of an exterior cured elastomer composition having at least a second exterior optical characteristic ingredient, the at least a second exterior optical characteristic ingredient different than the interior cured elastomer composition first interior optical characteristic ingredient, wherein with an elastomer void crack propagating from the exterior surface inward towards the interior elastomer region and a repeated rotary wing aircraft relative motion between the first rotary wing aircraft member and the second rotary wing aircraft member generates a plurality of interior cured elastomer composition crumbs to be expelled from the elastomer void, the interior cured elastomer composition crumbs optically distinguishable from the exterior cured elastomer composition.

In an embodiment the invention includes a method of making a rotary wing aircraft bearing to provide a constrained relative motion between a first rotary wing aircraft member and a second rotary wing aircraft member. The method includes providing a plurality of nonelastomeric shim members. The method includes providing a plurality of elastomeric shim member layers. The method includes providing at least one of the elastomeric shim member layers with an interior elastomer region, the interior elastomer region comprised of an interior elastomer composition having at least a first interior optical characteristic, and an exterior elastomer region, the exterior elastomer region comprised of an exterior elastomer composition having at least a second exterior optical characteristic, the at least a second exterior optical characteristic different than the interior elastomer composition first interior optical characteristic, with the exterior elastomer region disposed out from the interior elastomer region. The method including bonding the nonelastomeric shim members and the elastomeric shim member layers together to provide an alternating laminated bearing stack with the exterior elastomer region exterior of the interior elastomer region, the exterior elastomer region proximate an exterior surface of the alternating laminated bearing stack, the exterior elastomer region comprised of an exterior cured elastomer composition, the at least second exterior optical characteristic different than the interior cured elastomer composition first interior optical characteristic, wherein with an elastomer void crack propagating from the exterior surface inward towards the interior elastomer region and a repeated rotary wing aircraft relative motion between the first rotary wing aircraft member and the second rotary wing aircraft member generates a plurality of interior cured elastomer composition crumbs to be expelled from the elastomer void, the interior cured elastomer composition crumbs optically distinguishable from the exterior cured elastomer composition.

In an embodiment the invention includes a rotary wing aircraft bearing to provide a rotary wing motion between a first rotary wing aircraft member and a second rotary wing aircraft member. The bearing including an elastomeric bonded laminated bearing stack, the elastomeric bonded laminated bearing stack including a plurality of bonded alternating layers of nonelastomeric shim member layers and elastomeric shim members layers. The bearing including a predetermined first elastomeric shim member layer comprised of a first elastomer region, the first elastomer region comprised of a first cured elastomer composition having at least a first optical characteristic. The predetermined first elastomeric shim member layer comprised of a second elastomer region, the second elastomer region proximate an exterior surface, the second elastomer region comprised of a second cured elastomer composition having at least a second optical characteristic, the at least second optical characteristic different than the first cured elastomer composition first optical characteristic, wherein a rotary wing motion elastomer void crack propogating from the exterior surface inward towards an interior of the bearing interior elastomer region with the rotary wing motion generates a plurality of first cured elastomer composition crumbs expelled from the elastomer void, the first cured elastomer composition crumbs optically distinguishable from the second cured elastomer composition.

In an embodiment the invention includes a bearing to provide a constrained relative motion between a first member and a second member. The bearing includes an elastomeric mold bonded bearing stack, the elastomeric mold bonded bearing stack including at least a first mold bonded elastomeric shim layer, the at least first mold bonded elastomeric shim layer having an exterior surface and an interior center distal from the exterior surface. The elastomeric shim layer is comprised of an enclosed interior elastomer region distal from the exterior surface, the interior elastomer region comprised of an interior cured elastomer composition having at least a first interior optical characteristic ingredient. The elastomeric shim layer is comprised of an exterior elastomer region encompassing the interior elastomer region, the exterior elastomer region proximate the exterior surface, the exterior elastomer region comprised of an exterior cured elastomer composition having at least a second exterior optical characteristic ingredient, the at least second exterior optical characteristic ingredient different than the interior cured elastomer composition first interior optical characteristic ingredient, wherein an elastomer void crack propogating from the exterior surface inward towards the interior elastomer region and a repeated relative motion between the first member and the second member generates a plurality of interior cured elastomer composition crumbs to be expelled from the elastomer void, the interior cured elastomer composition crumbs optically distinguishable from the exterior cured elastomer composition. Preferably the interior cured elastomer composition crumbs come from the interior cured elastomer composition, preferably the solid interior cured elastomer is broken up into crumbs with the repeated relative motion proximate an interior portion of the propogating crack and expelled outward towards the exterior, with the interior cured elastomer composition crumbs optically distinguishable from exterior cured elastomer composition crumbs and the exterior cured elastomer surface. Preferably the bearing is installed in a bearing location for bearing a compressive load between the first member and the second member in a first direction and the repeated relative motion comprises an alternating shear load in a first and second shearing direction with the compressive load first direction nonparallel to the first and second shearing direction. Preferably when installed the interior elastomer crumbs are visible by an observing inspector. Preferably the expelled interior cured elastomer composition crumbs are persistent with the crumbs preferably collecting and sticking to the exterior surface, and preferably persistent to an exposed fluid stream, preferably with the expelled interior cured elastomer composition crumbs sticking the exterior surface when the bearing is moving through air or exposed to a water stream/current. Preferably the at least one elastomeric shim layer is visible by an observing inspector when installed in a bearing location for bearing a compressive load between the first member and the second member in a first direction and the repeated relative motion comprises an alternating shear load in a first and second shearing direction with the compressive load first direction nonparallel to the first and second shearing direction. Preferably the at least one elastomeric shim layer has an elastomer layer thickness t and an exterior surface bulge area BA, with the elastomeric shim layer having a bonded elastomer interface load area LA, with the elastomeric shim layer having a shape factor SF with $0.1<SF<60$. Preferably the at least one elastomeric shim layer with the interior elastomer region interior cured elastomer composition and the exterior elastomer region exterior cured elastomer composition are disposed at a predetermine degradation position within the bearing stack and the exterior elastomer region extends inward towards the interior elastomer region with a predetermined exterior elastomer region radial dimension. Preferably the bearing is a rotary wing aircraft bearing for a rotary wing aircraft.

In an embodiment the invention includes a method of making a bearing to provide a constrained relative motion between a first member and a second member. The method includes providing at least a first nonelastomeric member surface and at least a second nonelastomeric member surface. The method includes providing at least a first elastomeric shim layer between the first nonelastomeric member surface and the at least second nonelastomeric member surface in a mold, and bonding the first elastomeric shim layer to the first nonelastomeric member surface and the second nonelastomeric member surface in the mold to provide an elastomeric mold bonded bearing stack, with first mold bonded elastomeric shim layer having an exterior surface and an interior center distal from the exterior surface, the elastomeric shim layer comprised of an enclosed interior bonded elastomer region distal from the exterior surface, the interior elastomer region comprised of an interior cured elastomer composition having at least a first interior optical characteristic ingredient, and the elastomeric shim layer comprised of an exterior bonded elastomer region encompassing the interior bonded elastomer region, the exterior elastomer region proximate the exterior surface, the exterior elastomer region comprised of an exterior cured elastomer composition having at least a second exterior optical characteristic ingredient, the at least second exterior optical characteristic ingredient different than the interior cured elastomer composition first interior optical characteristic ingredient, wherein an elastomer void crack propogating from the exterior surface inward towards the interior elastomer region and a repeated relative motion between the first member and the second member generates a plurality of interior cured elastomer composition crumbs to be expelled from the elastomer void, the interior cured elastomer composition crumbs optically distinguishable from the exterior cured elastomer composition. Preferably the interior cured elastomer composition crumbs come from the interior cured elastomer composition, preferably with the solid interior cured elastomer broken up into crumbs with the repeated relative motion proximate an interior portion of the propogating crack and expelled outward towards the exterior, with the interior cured elastomer composition crumbs optically distinguishable from exterior cured elastomer composition crumbs and the exterior surface. Preferably the bearing is installed in a bearing location for bearing a compressive load between the first member and the second member in a first direction and the repeated relative motion comprises an alternating shear load in a first and second shearing direction with the compressive load first direction nonparallel to the first and second shearing direction. Preferably the expelled interior cured elastomer composition crumbs are persistent in that they preferably collect and stick to the exterior surface, and preferably persistent to an exposed fluid stream, preferably with the expelled interior cured elastomer composition crumbs sticking to the exterior surface when the bearing is moving through air or exposed to a water stream/current. Preferably the at least one elastomeric shim layer is visible by an observing inspector when installed in a bearing location for bearing a compressive load between the first member and the second member in a first direction and the repeated relative motion comprises an alternating shear load in a first and second shearing direction with the compressive load first direction nonparallel to the first and second shearing direction. Preferably the at least one elastomeric shim layer has an elastomer layer thickness t and an exterior surface bulge area BA, with the elastomeric shim layer having a bonded elastomer interface load area LA, with the elastomeric shim layer having a shape factor SF with $0.1<SF<60$. Preferably the at least one elastomeric shim layer with the interior elastomer region interior cured elastomer composition and the exterior elastomer region exterior cured elastomer composition are disposed at a predetermine degradation position within the bearing stack and the exterior elastomer region extends inward towards the interior elastomer region with a predetermined exterior elastomer region radial dimension. Preferably the bearing is a rotary wing aircraft bearing for a rotary wing aircraft, with the bearing installed in a rotary wing system of a rotary wing aircraft.

It is to be understood that both the foregoing general description and the following detailed description are exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principals and operation of the invention.

BRIEF DESCRIPTION OF THE DRAWINGS

The patent or application file contains at least one drawing photograph executed in color. Copies of this patent or patent application publication with color drawing(s) will be provided by the Office upon request and payment of the necessary fee.

FIG. 1A-C illustrate rotary wing aircraft bearings providing constrained relative motion between rotary wing aircraft members.

FIG. 2A-B illustrate cross section views of elastomeric mold bonded laminated bearing stacks with multiple alternating layers of nonelastomeric shim member layers and elastomeric shim members with an interior elastomer region having at at least a first interior optical characteristic different than the exterior elastomer region.

FIG. 3A-B illustrate interior and exterior elastomer region materials with the interior elastomer composition having at least a first interior optical characteristic different than the exterior elastomer region, with the elastomer region materials shown before they are bonded and cured into an elastomeric shim member layer.

FIG. 4 illustrates a rotary wing aircraft bearing with non-black colored elastomer on the outside exterior surface of two elastomeric shim members layers.

FIG. 5A-B illustrate photographs taken after cycles of torsion repeated rotary wing motion fatigue tests with expelled crumbs from the interior elastomer region optically distinguishable from the exterior elastomer.

FIG. 7 is a color photgraph showing brown crumbs 46 expelled from the interior red brown elastomer region, with such optically distinguishable from the exterior black elastomer after the torsion repeated rotary wing motion fatigue test of the sample.

FIG. 8 is a color photgraph showing black crumbs 46 expelled from the interior black elastomer region, with such optically distinguishable from the exterior white elastomer after the torsion repeated rotary wing motion fatigue test of the sample.

FIG. 9 illustrates mold bonding nonelastomeric shim members and elastomeric shim member layers together to provide an alternating laminated bearing stack with an exterior elastomer region and an interior center elastomer region in a mold with a transfer elastomer sprue proximate the interior center region with the transferred elastomer in common with the nontransferred interior elastomer region shim layers which are layed up between the nonelastomeric shim member layers.

FIG. 10 illustrates mold bonding nonelastomeric shim members and elastomeric shim member layers together to provide an alternating laminated bearing stack with an exterior elastomer region and an interior center elastomer region in a mold with transfer elastomer sprues proximate the exterior region with the transferred elastomer in common with the nontransferred exterior elastomer region shim layers which are layed up between the nonelastomeric shim member layers.

FIG. 16 illustrates views of a bearing with an interior elastomer region with optical characteristics different than the exterior elastomer region.

FIG. 17 illustrates views of a bearing with an interior elastomer region with optical characteristics different than the exterior elastomer region.

DETAILED DESCRIPTION OF THE PREFERRED EMBODIMENT

Figure 1B:
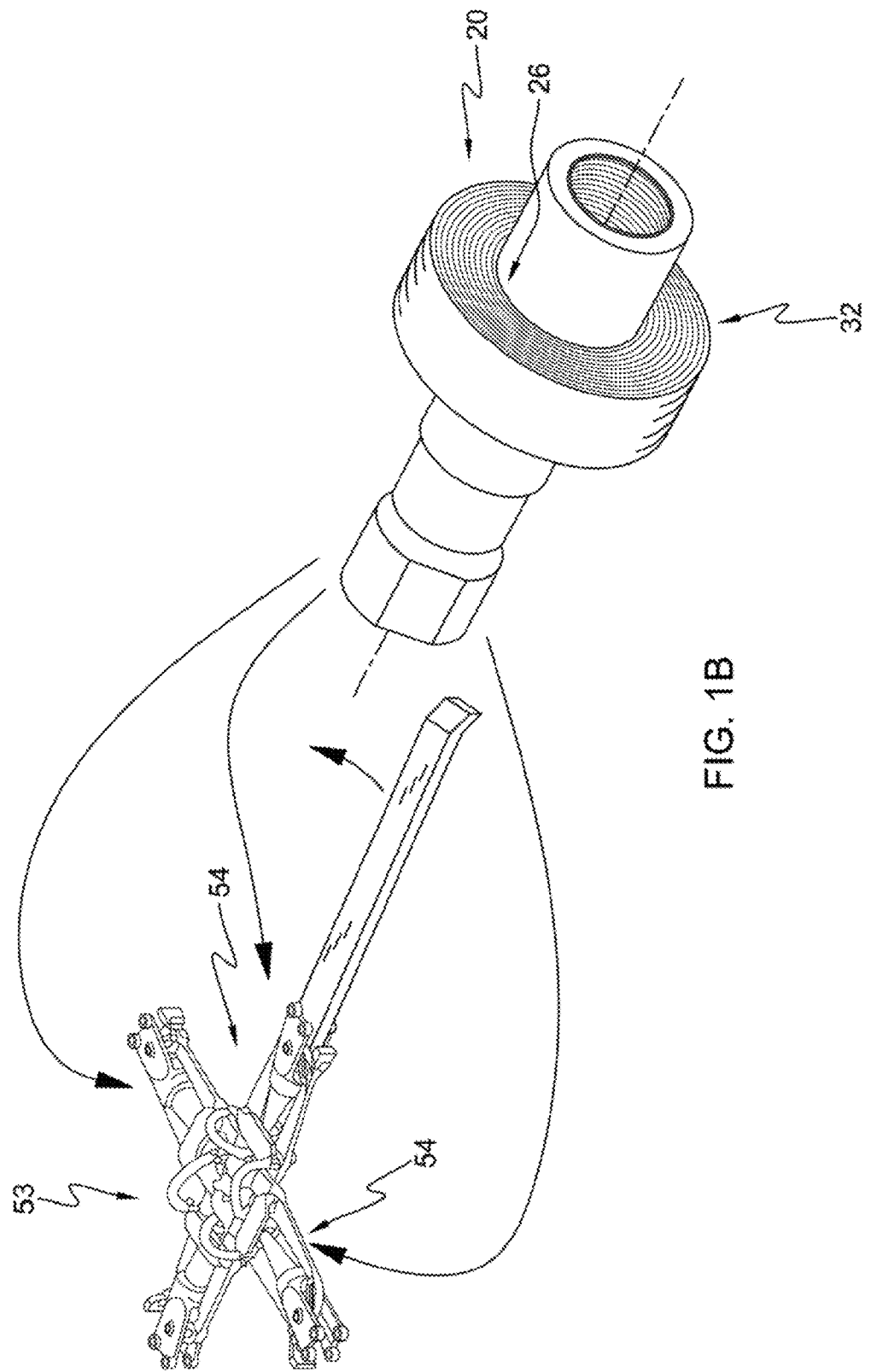

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

Reference will now be made in detail to the present preferred embodiments of the invention, examples of which are illustrated in the accompanying figures.

In an embodiment the invention includes a rotary wing aircraft bearing to provide a constrained relative motion between a first rotary wing aircraft member and a second rotary wing aircraft member. The bearing including an elastomeric mold bonded laminated subassembly bearing stack, the elastomeric mold bonded laminated subassembly bearing stack including a plurality of mold bonded alternating layers of nonelastomeric shim member layers and elastomeric shim members layers, the alternating layers having an exterior surface and an interior center distal from the exterior surface. At least one of the elastomeric shim member layers comprised of an interior elastomer region distal from the exterior surface, the interior elastomer region comprised of an interior cured elastomer composition having at least a first interior optical characteristic ingredient, and an exterior elastomer region encompassing the interior elastomer region, the exterior elastomer region proximate the exterior surface, the exterior elastomer region comprised of an exterior cured elastomer composition having at least a second exterior optical characteristic ingredient, the at least second exterior optical characteristic ingredient different than the interior cured elastomer composition first interior optical characteristic ingredient, wherein with an elastomer void crack propogating from the exterior surface inward towards the interior elastomer region and a repeated rotary wing aircraft relative motion between the first rotary wing aircraft member and the second rotary wing aircraft member generates a plurality of interior cured elastomer composition crumbs to be expelled from the elastomer void, the interior cured elastomer composition crumbs optically distinguishable from the exterior cured elastomer composition. In an embodiment a plurality of the elastomeric shim member layers include an interior elastomer region with the interior first optical characteristic and all of the elastomeric shim member layers exterior elastomer regions are optically distinguishable from the interior elastomer regions. In an embodiment only predetermined elastomeric shim member layers include the at least first interior and second exterior optically distinguishable characteristics. In embodiments the rotary wing aircraft bearing first interior optical characteristic ingredient is comprised of a dye, preferably an activated dye. Preferably the dye is not soluble in the interior cured elastomer. Preferably the dye is water soluble, preferably with the water soluble dye activated by an inspection fluid. Preferably the dye is fluorescent. Preferably the non-elastomer-soluble dye is a water soluble dye that is fluorescent wherein an inspection fluid applied to the bearing discloses the first interior elastomer composition. In an embodiment the first interior optical characteristic ingredient is comprised of a carbon black substitute. In an embodiment the carbon black substitute is comprised of silica. Preferably the carbon black substitute composition includes a nonblack colorant. In an embodiment the first interior optical characteristic ingredient is comprised of carbon black and the second exterior composition is comprised of a carbon black substitute. In an embodiment the second exterior optical characteristic is comprised of carbon black. In an embodiment the exterior elastomer region extends inward towards the bearing layer's center normal axis towards the interior elastomer region with a predetermined exterior elastomer region radial dimension. Preferably the exterior elastomer region extends inward at least 10% of the total layer radial dimension, preferably at least 13% of the total layer radial dimension, preferably at least 16% of the total layer radial dimension, preferably at least 19% of the total layer radial dimension, preferably at least 21% of the total layer radial dimension, preferably at least 25% of the total layer radial dimension. Preferably the interior elastomer region extends outward towards bearing exterior surface and the exterior elastomer region with a predetermined interior elastomer region radial dimension. Preferably the interior elastomer region is centered about a bearing center axis, with the interior elastomer region extending outward from the bearing center axis towards bearing exterior surface with a predetermined interior elastomer region dimension. Preferably the center axis is substantially through the center of the alternating layers, preferably substantially normal to the alternating layers. Preferably the at least one elastomeric shim member layer with the interior elastomer region interior cured elastomer composition and the exterior elastomer region exterior cured elastomer composition are disposed at a predetermined initial early degradation position within the laminated bearing stack. Preferably the at least one elastomeric shim member layer at the predetermined initial early degradation position within the laminated bearing stack is visible by an observing inspector when installed in the rotary wing aircraft. Preferably the at least one elastomeric shim member layer with the interior elastomer region interior cured elastomer composition and the exterior elastomer region exterior cured elastomer composition are disposed at a predetermine degradation position within the laminated bearing stack includes a third elastomer region cured elastomer composition having a third optical characteristic different from the interior elastomer region interior cured elastomer composition and the exterior elastomer region exterior cured elastomer composition.

In an embodiment the invention includes a method of making a rotary wing aircraft bearing to provide a constrained relative motion between a first rotary wing aircraft member and a second rotary wing aircraft member. The method includes providing a plurality of nonelastomeric shim members. The method includes providing a plurality of elastomeric shim member layers, at least one predetermined elastomeric shim member layer has an interior elastomer region, the interior elastomer region comprised of an interior elastomer composition having at least a first interior optical characteristic with a first interior optical characteristic ingredient. The at least one predetermined elastomeric shim member layer having an exterior elastomer region, the exterior elastomer region comprised of an exterior elastomer composition having at least a second exterior optical characteristic with a second interior optical characteristic ingredient, the at least second exterior optical characteristic ingredient different than the interior elastomer composition first interior optical characteristic ingredient, the exterior elastomer region disposed out from the interior elastomer region and encompassing the interior elastomer. The method includes mold curing elastomer bonding the nonelastomeric shim members and the elastomeric shim member layers together to provide an alternating laminated bearing stack with the exterior elastomer region exterior of the interior elastomer region, the exterior elastomer region proximate an exterior surface of the alternating laminated bearing stack. The bonded exterior elastomer region comprised of an exterior cured elastomer composition, the at least second exterior optical characteristic different than the interior cured elastomer composition first interior optical characteristic, wherein an elastomer void crack propagating from the exterior surface inward towards the interior elastomer region with a repeated rotary wing aircraft relative motion between the first rotary wing aircraft member and the second rotary wing aircraft member generates a plurality of interior cured elastomer composition crumbs to be expelled from the elastomer void, the interior cured elastomer composition crumbs optically distinguishable from the exterior cured elastomer composition. Preferably the method includes installing the rotary wing aircraft bearing in a rotary wing aircraft with an observable portion of the exterior elastomer region visible to an inspector wherein the optically distinguishable interior cured elastomer composition crumbs are visually detected by the inspector. Preferably with the method a plurality of the elastomeric shim member layers include an interior elastomer region. Preferably with the method a plurality of the elastomeric shim member layers include an interior elastomer region and all of the elastomeric shim member layers exterior elastomer regions are optically distinguishable from these interior elastomer regions. In an embodiment the first interior optical characteristic ingredient is comprised of a dye, preferably an activated dye. Preferably the dye is not soluble in the interior elastomer, preferably with the dye water soluble. Preferably the dye is fluorescent, preferably with the water activated dye fluorescent when an inspecting water inspection fluid is applied to the bearing. In an embodiment the first interior optical characteristic ingredient is comprised of a carbon black substitute, preferably with the carbon black substitute comprised of silica. Preferably with the carbon black substitute the elastomer composition ingredients include a nonblack colorant. In an embodiment the first interior optical characteristic ingredient is comprised of carbon black. In an embodiment the second exterior optical characteristic ingredient is comprised of carbon black. In an embodiment the second exterior optical characteristic ingredient is comprised of a carbon black substitute. Preferably the exterior elastomer region extends inward towards bearing layer normal center axis and towards the interior elastomer region with a predetermined exterior elastomer region radial dimension, preferably the exterior elastomer region extends inward at least 10% of the total layer radial dimension, preferably at least 13% of the total layer radial dimension, preferably at least 16% of the total layer radial dimension, preferably at least 19% of the total layer radial dimension, preferably at least 21% of the total layer radial dimension, preferably at least 25% of the total layer radial dimension. Preferably the interior elastomer region extends outward towards the bearing exterior surface and towards the exterior elastomer region with a predetermined interior elastomer region radial dimension. Preferably the interior elastomer region is centered about a bearing center axis, with the interior elastomer region extending outward from the bearing center axis and towards the bearing exterior surface with a predetermined interior elastomer region dimension, preferably with the center axis substantially through the center of the alternating layers and substantially normal to the alternating layers. Preferably the at least one elastomeric shim member layer with the interior elastomer region interior cured elastomer composition and the exterior elastomer region exterior cured elastomer composition are disposed at a predetermine initial early degradation position within the laminated bearing stack, preferably with the at least one elastomeric shim member layer at the predetermine degradation position within the laminated bearing stack visible by an observing inspector when installed in a rotary wing aircraft. In an embodiment the at least one elastomeric shim member layer includes a third elastomer region cured elastomer composition having a third optical characteristic different from the interior elastomer region interior cured elastomer composition and the exterior elastomer region exterior cured elastomer composition. Preferably the nonelastomeric shim members and the elastomeric shim member layers are bonded together in a mold with the elastomeric shim member layers cured inside the mold. Preferably the mold includes an elastomer transfer sprue for transferring additional elastomer into the mold. In first preferred embodiment the elastomer transfer sprue is proximate the interior elastomer region and the additional elastomer appears optically similar to the interior elastomer composition. In a second preferred embodiment the elastomer transfer sprue is proximate the exterior elastomer region and the additional elastomer appears optically similar to the exterior elastomer composition.

In an embodiment the invention includes a rotary wing aircraft bearing to provide a constrained relative rotary wing motion between a first rotary wing aircraft member and a second rotary wing aircraft member. The bearing includes an elastomeric bonded laminated bearing stack, the elastomeric bonded laminated bearing stack including a plurality of bonded alternating layers of nonelastomeric shim member layers and elastomeric shim members layers, with a predetermined first elastomeric shim members layer comprised of a first elastomer region, the first elastomer region comprised of an first cured elastomer composition having at least a first optical characteristic, and a second elastomer region, the second elastomer region proximate an exterior surface, the second elastomer region comprised of a second cured elastomer composition having at least a second optical characteristic, the at least second optical characteristic elastomer having an at least second optical characteristic ingredient different than the first cured elastomer composition first optical characteristic ingredient, wherein a rotary wing motion elastomer void crack propagating from the exterior surface inward towards an interior of the bearing interior elastomer region with the rotary wing motion generates a plurality of first cured elastomer composition crumbs expelled from the elastomer void, the first cured elastomer composition crumbs optically distinguishable from the second cured elastomer composition. Preferably the predetermined first elastomeric shim layer has a predetermined stack position within elastomeric bonded laminated bearing stack, preferably determined from historical testing and design.

Preferably the at least two different optically visually distinguishable rubber elastomers are embedded and bonded within the at least one predetermined individual layers of the High Capacity Laminated elastomeric bearing, with the bonded elastomer shim member with layer the at least two different optically visually distinguishable rubber elastomers preferably thin, preferably with a thickness less than 0.200 inches, preferably less than 150 inches. Preferably as the HCL bearings fail a crack progress inward from the surface into the thin rubber layers, and as the crack progresses, crumbs of the cracked rubber are carried to the surface of the part where they can be visually observed, and with the at least second different optically visually distinguishable rubber elastomer embedded inside the layer as visually contrasting rubber regions at predetermined internal depths, the crack depth in the HCL bearing can be monitored by observing the optical difference of the crumbs of expelled elastomer at the surface.

In preferred embodiments the elastomer compositions are based on diene rubber, preferrably natural rubber, polyisoprene, polybutadiene, styrene butadiene and blends thereof. The elastomers are formulated to be nonoptically similar and compatible so they can be cured together as one shim layer, but visually distinct, either under human visible light or other electromagnetic spectrum wavelengths such as under ultraviolet light. For example, one elastomer may be reinforced with carbon black and another by precipitated or fumed silica as a carbon black substitute. When using silica as a carbon black substitute, it is preferred to include a silane coupling agent to increase the interaction between the silica and the polymer. The silica-reinforced elastomer composition is preferrably colored by adding either organic or inorganic pigments or dyes. In embodiments the elastomer compositions are provided with optically different characteristics with optical characteristic ingredients such as made white through the addition of titanium dioxide, rust brown red with red iron oxide, green with chromium oxide or with green phthalocyanine. In embodiments pigments or dyes including fluorescent pigment dyes are used. Preferably rubber pigments and dyes are used to create visually distinct rubber compositions. In an embodiment the visually distinguishable optical characteristic ingredient is a water soluble form of fluorescein (called sodium fluorescein or uranine yellow). Sodium fluorescein is not soluble in elastomer rubber but it is readily soluble in water and produces an intense yellow-green color when rubber containing sodium fluorescein comes in contact with water. The inclusion of sodium fluorescein in the interior elastomer region gives a strong visual evidence of crack depth when the rubber crumbs or the crack itself is exposed to water and turns the water yellow. Expelled interior crumbs are preferably inspected for by water activation by exposing the expelled elastomer crumbs to water, such as with water flushing, water spray, or wiping with a wet material. In a preferred embodiment the inclusion of sodium fluorescein in the interior elastomer region is in a bearing with a elastomeric shim layer with the bearing installed in a water environment bearing location.

Below are examples of optically visually distinguishable rubber elastomers with different visually distinguishable optical characteristic ingredients:

| Ingredient | Optical Character color | | | | | |
|---|---|---|---|---|---|---|
| | Black | Red | White | Yellow | Green | Black with Yellow Indicator |
| Natural rubber | 60.0 | 60.0 | 60.0 | 60.0 | 60.0 | 60.0 |
| Polybutadiene rubber | 30.0 | 30.0 | 30.0 | 30.0 | 30.0 | 30.0 |
| Styrene butadiene rubber | 10.0 | 10.0 | 10.0 | 10.0 | 10.0 | 10.0 |
| Aromatic oil | 5.0 | 5.0 | 5.0 | 5.0 | 5.0 | 5.0 |
| Stearic acid | 2.0 | 2.0 | 2.0 | 2.0 | 2.0 | 2.0 |
| Zinc oxide | 5.0 | 5.0 | 5.0 | 5.0 | 5.0 | 5.0 |
| Sulfur | 1.8 | 1.8 | 1.8 | 1.8 | 1.8 | 1.8 |
| CBTS (accelerator) | 1.2 | 1.2 | 1.2 | 1.2 | 1.2 | 1.2 |
| Si-69 Silane | — | 5.0 | 5.0 | 5.0 | 5.0 | — |
| N330 carbon black | 45.0 | — | — | — | — | 45.0 |
| Hi-Sil 233 silica | — | 40.0 | 40.0 | 40.0 | 40.0 | — |
| Titanium dioxide | — | 8.0 | 5.0 | 2.0 | 5.0 | — |
| Red iron oxide | — | — | 1.0 | — | — | — |
| Chromium Green oxide | — | — | — | — | 2.0 | — |
| Yellow 2555 pigment | — | — | — | 2.5 | — | — |
| Sodium fluorescein | — | — | — | — | — | 5.0 |

Figure 2B:
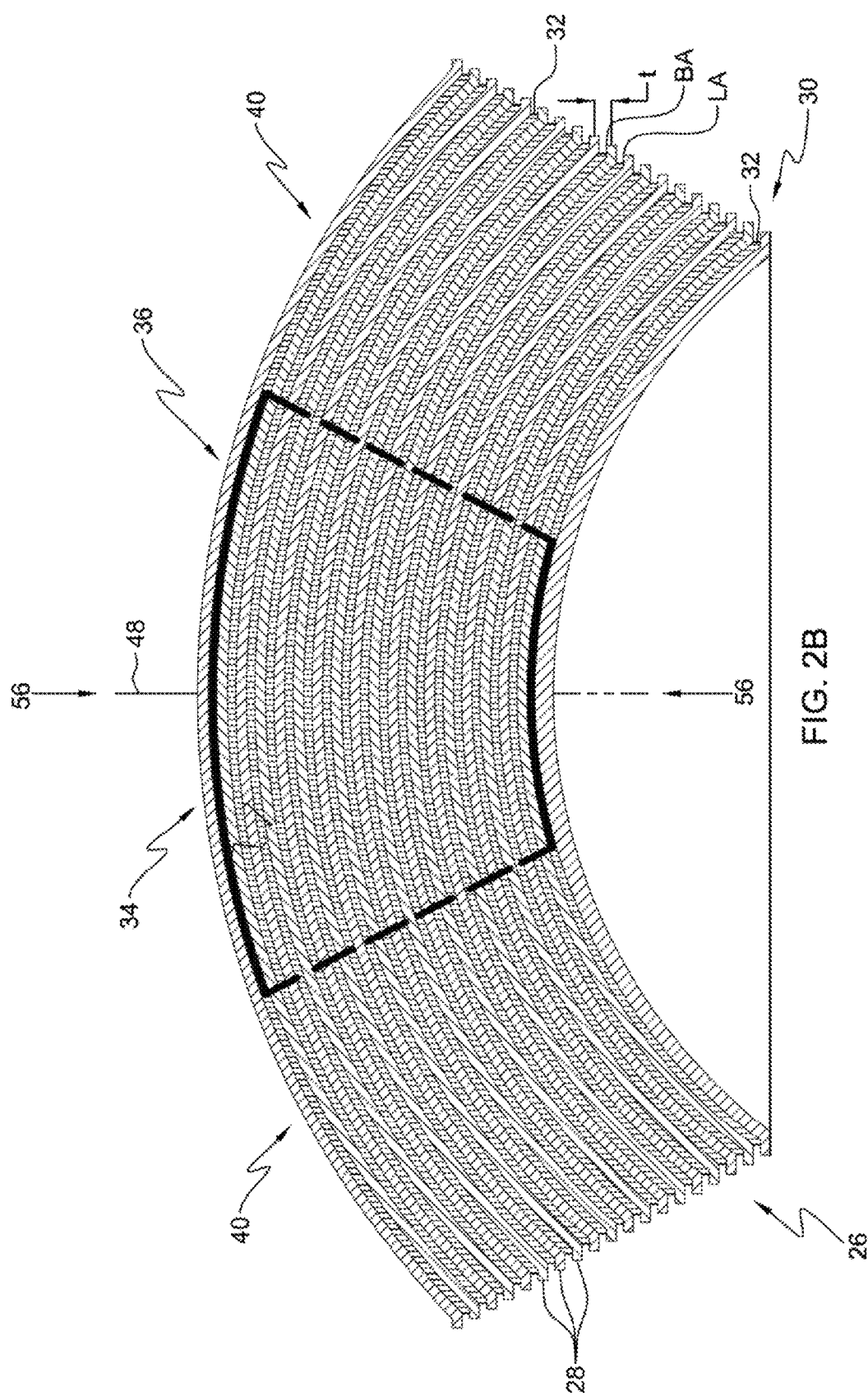
Figure 3A:
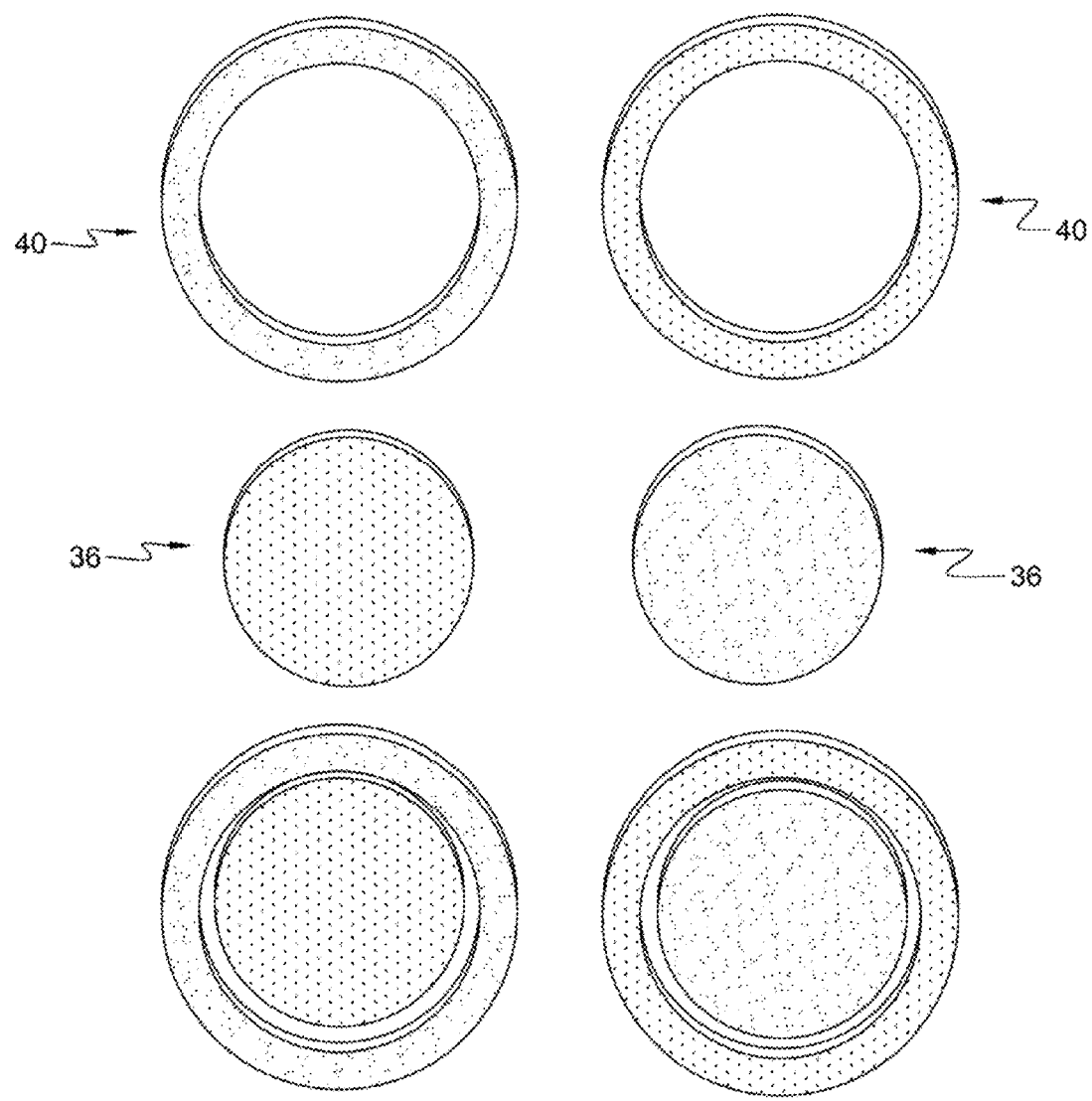
Figure 6:
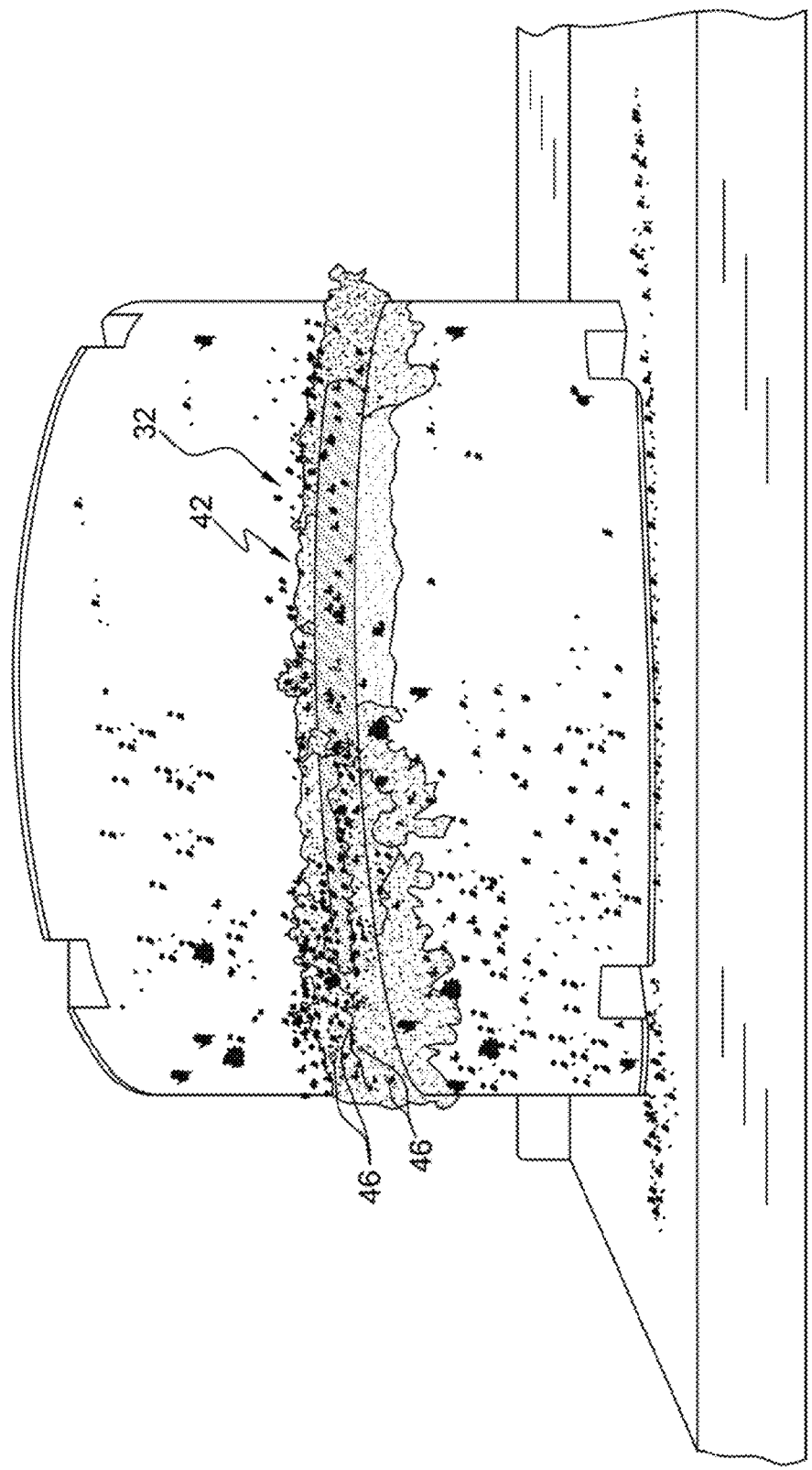
FIG. 6 illustrates a photograph taken after cycles of a torsion repeated rotary wing motion fatigue test with expelled white crumbs 46 from the interior elastomer region optically distinguishable from the exterior elastomer.
Figure 11:
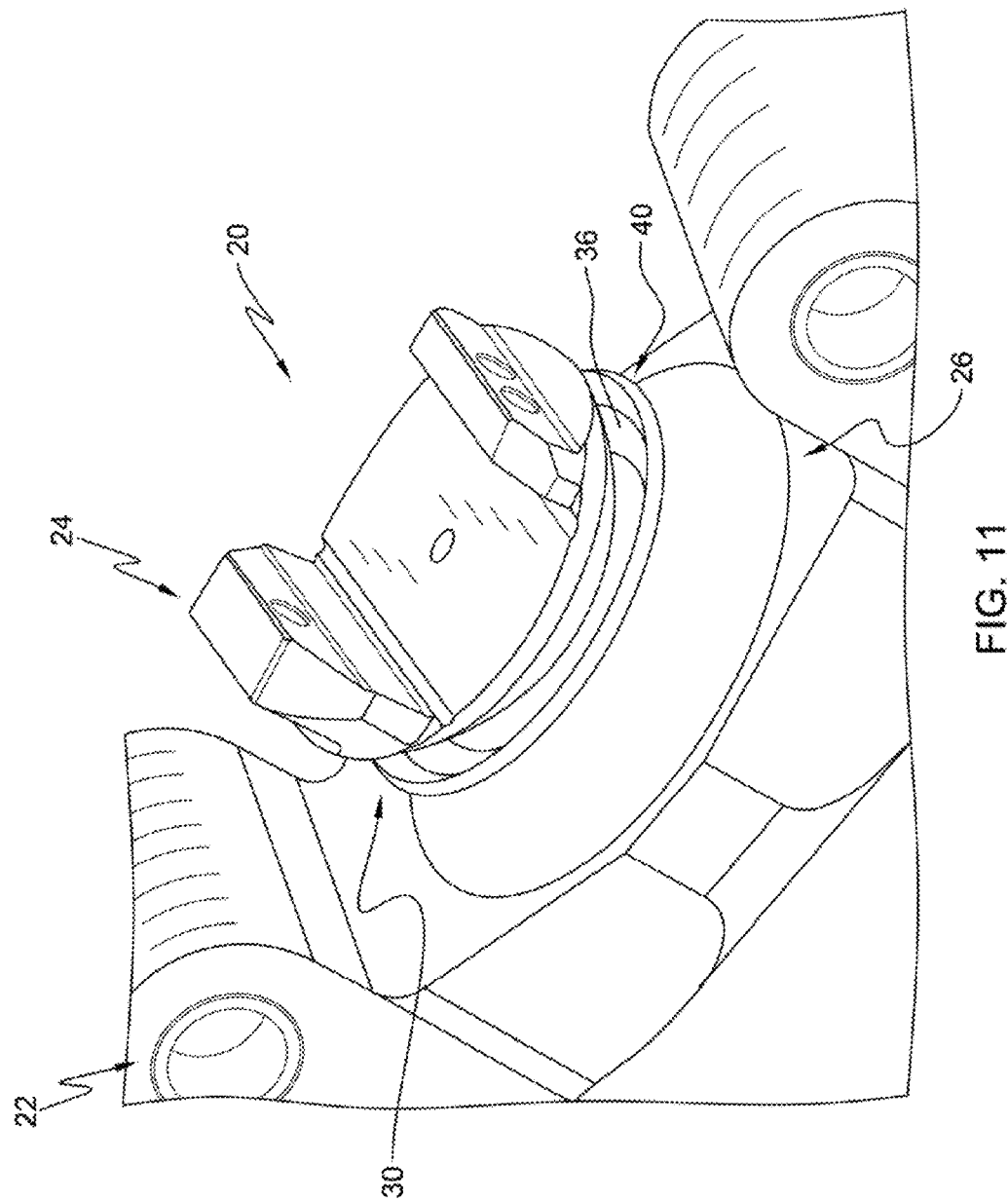
FIG. 11 illustrates a two color elastomer marker band placed in a predetermined layer of a rotary wing spherical bearing with the spherical bearing bonded bearing stack shadow ghosted to highlight the marker band of the interior/exterior elastomers.
Figure 12:
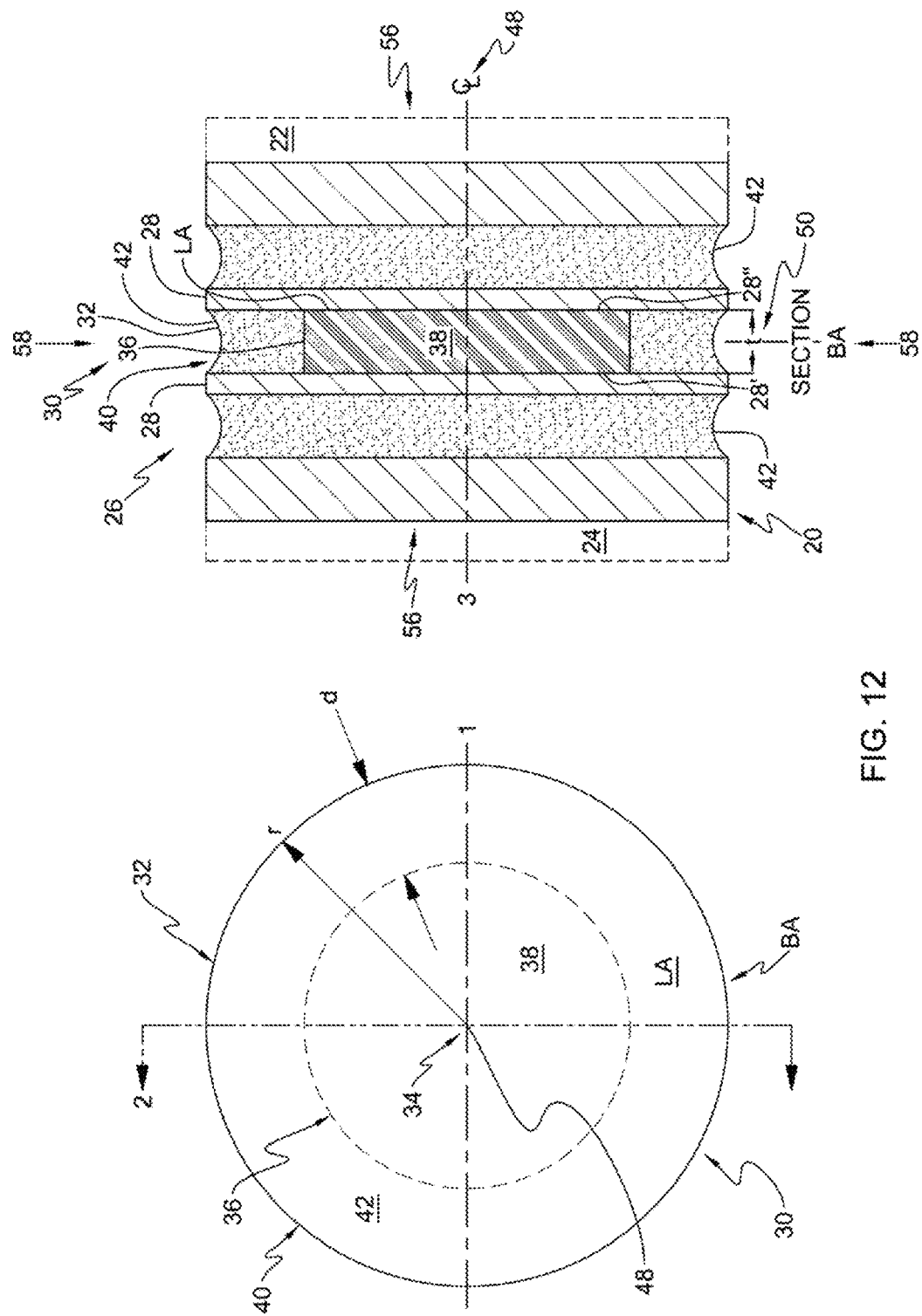
FIG. 12 illustrates views of a bearing with an interior elastomer region with optical characteristics different than the exterior elastomer region.
Figure 13:
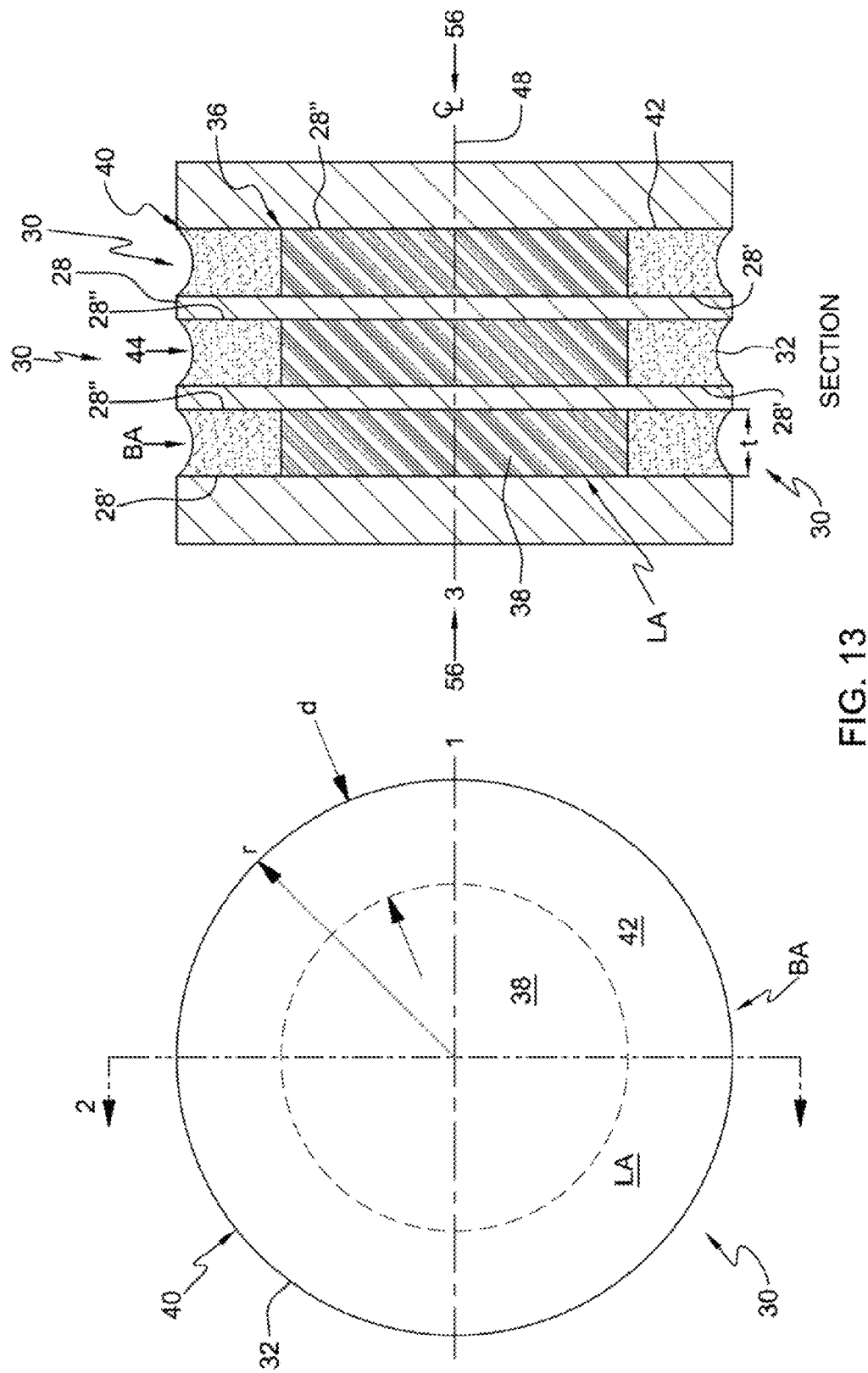
FIG. 13 illustrates views of a bearing with an interior elastomer region with optical characteristics different than the exterior elastomer region.
Figure 14:
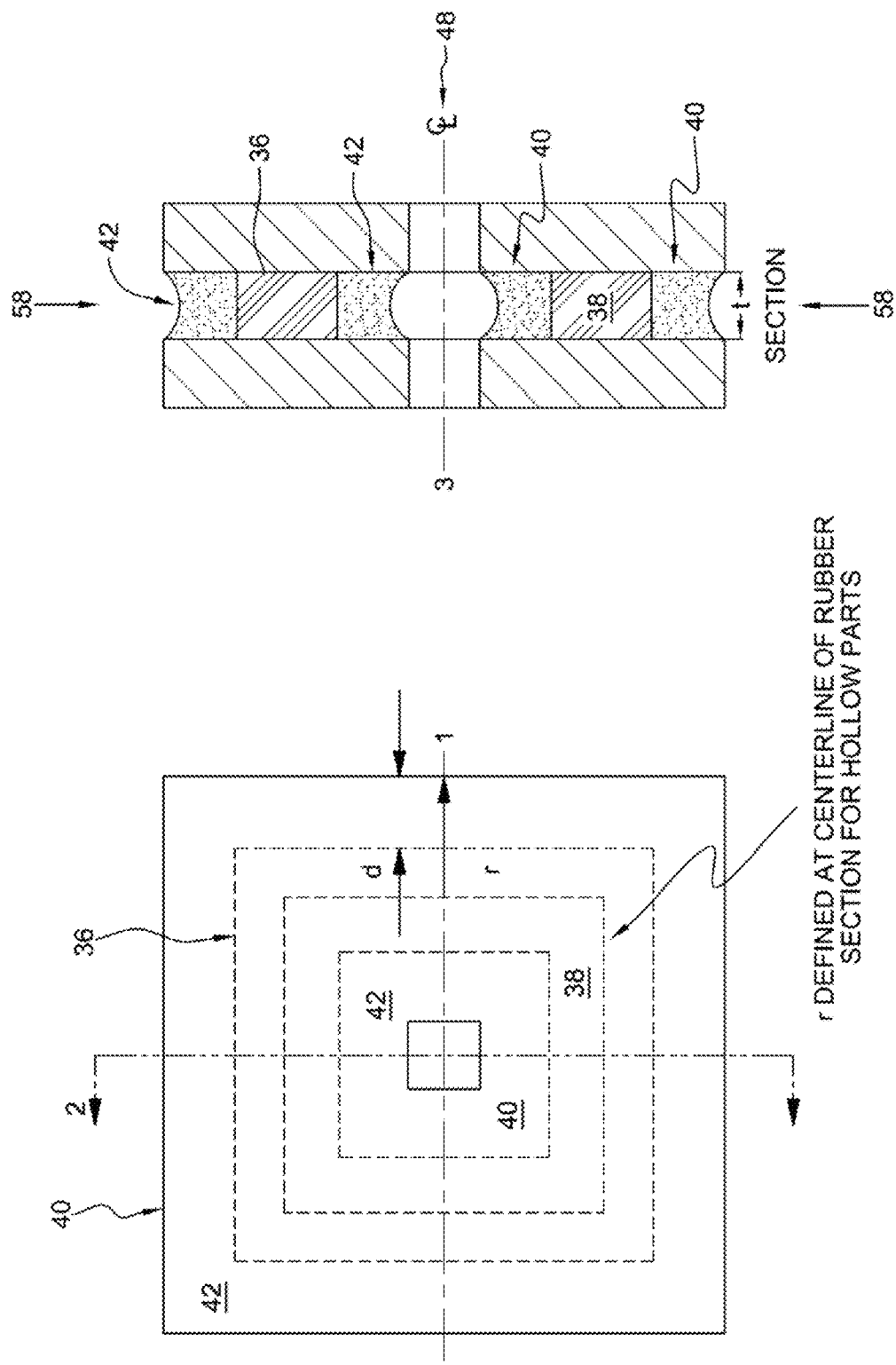
FIG. 14 illustrates views of a bearing with an interior elastomer region with optical characteristics different than the exterior elastomer region.
Figure 15:
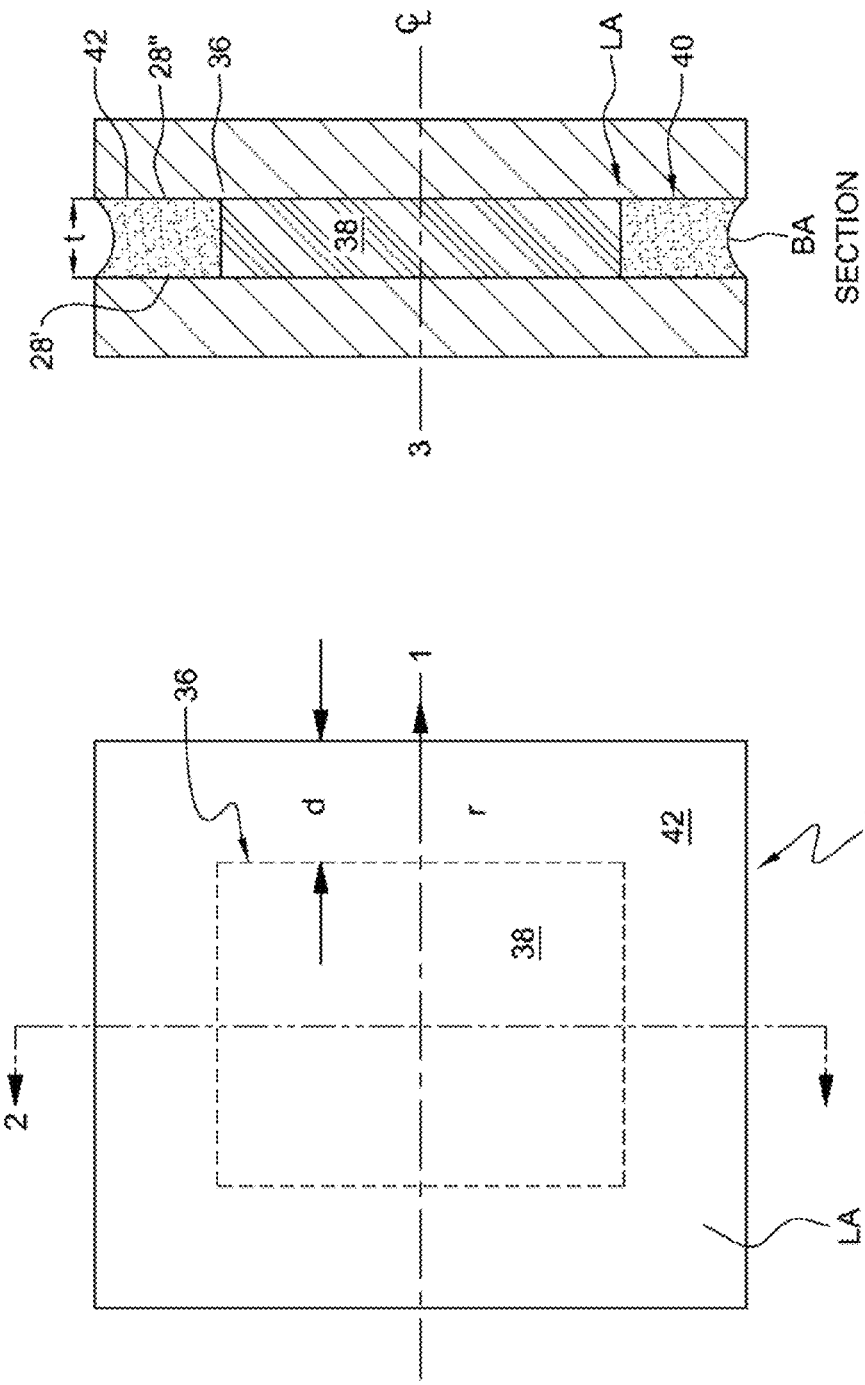
FIG. 15 illustrates views of a bearing with an interior elastomer region with optical characteristics different than the exterior elastomer region.
Figure 18:
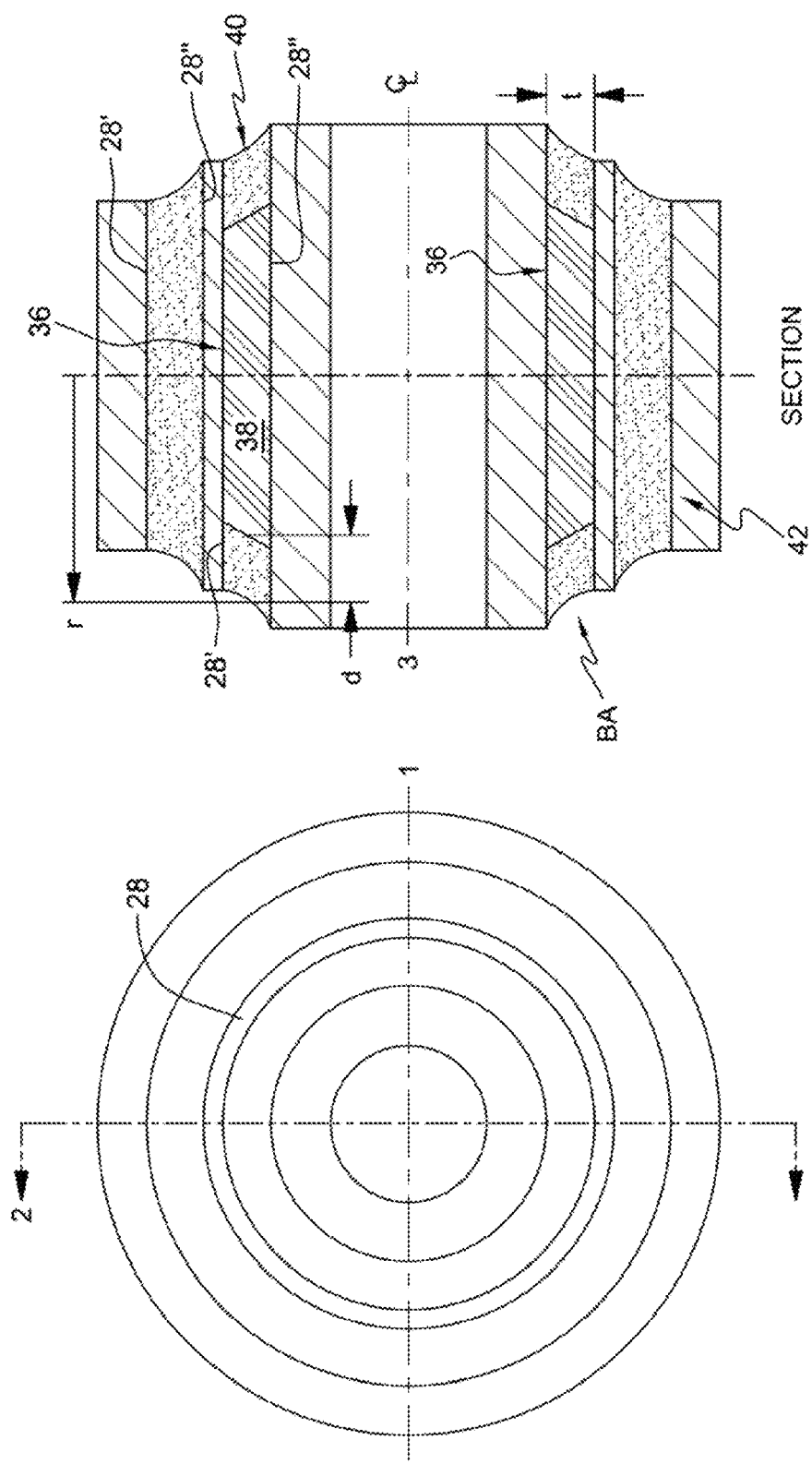
FIG. 18 illustrates views of a bearing with an interior elastomer region with optical characteristics different than the exterior elastomer region.
Figure 19:
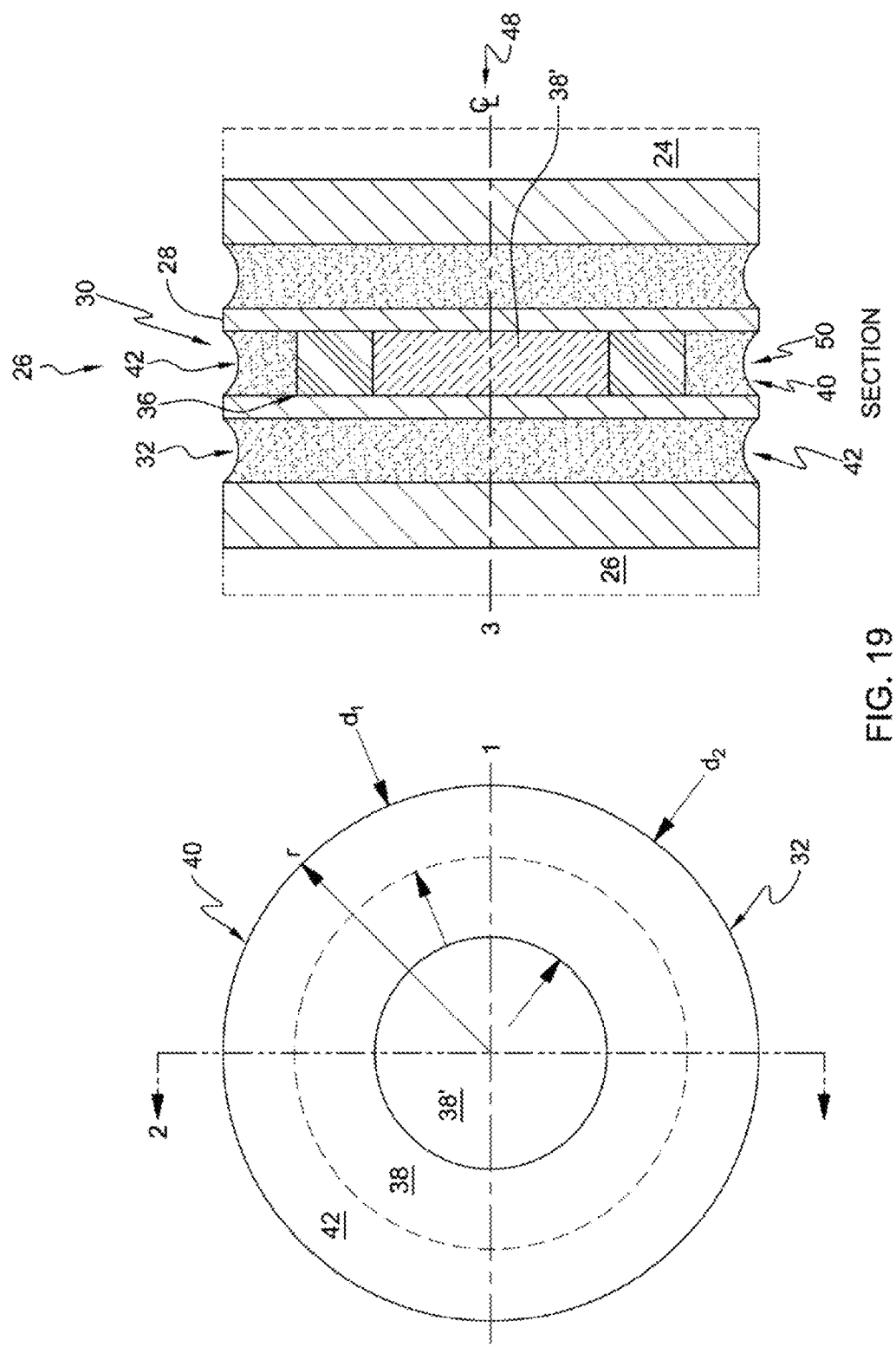
FIG. 19 illustrates views of a bearing with interior elastomer regions with optical characteristics different than the exterior elastomer region.

FIG. 1 illustrate rotary wing aircraft bearings with elastomeric mold bonded laminated bearing stacks, the elastomeric mold bonded laminated bearing stack including a plurality of mold bonded alternating layers of nonelastomeric shim member layers and elastomeric shim members layers, the alternating layers of the laminated bearing stack having an exterior surface and an interior center distal from the exterior surface. As illustrated in FIG. 2 at least one of said elastomeric shim members layers has an interior elastomer region distal from said exterior surface, the interior elastomer region comprised of an interior cured elastomer composition having at least a first interior optical characteristic different than the exterior elastomer region. FIG. 3 illustrates illustrate interior elastomer regions comprised of interior elastomer composition having at least a first interior optical characteristic different than the exterior elastomer region, with the elastomer regions shown before they are bonded and cured into an elastomeric shim member layer. FIG. 4 illustrates a rotary wing aircraft bearing with the non-black colored elastomer on the outside exterior surface of two elastomeric shim members layers. In this embodiment the visually distinguishable optical characteristic of the two exterior layers is yellow such that an inspector visually looks for black crumbs from the interior region of the layer accumulated on the yellow exterior. In this embodiment the yellow rubber exterior regions have been disposed in elastomer shim layers five and six of the stack with a depth extending inward into the bearing of ⅜ inch, in the rubber radial dimension range of about 10 to 25%. Elastomer shim layers five and six of the stack were predetermined and selected in that historical studies and testing had shown that these two layers (elastomer shim layers five and six of the stack) are prone to degradation and that bearing elastomeric damage should be expected to develop here first (intentionally targeted and predetermined degradation to occur here first). FIG. 5 illustrates an embodiment with a cured exterior black rubber region and an interior red brown cured elastomer region. FIG. 5A photograph was taken after 600 k cycles of a torsion repeated rotary wing motion fatigue test. FIG. 5B photograph was taken after 800 k cycles of the torsion repeated rotary wing motion test. The torsion repeated rotary wing motion test sample of FIG. 5 was constructed of a single bonded elastomeric shim layer with the fully bonded elastomer layer between the two nonelastomeric metal test ends tested with a high compression load applied by the two nonelastomeric test ends while the 600 k and 800 k torsion cycles are applied. The interior red brown cured elastomer region was provided with carbon black substitute silica and iron oxide. FIG. 6 illustrates white crumbs from the interior white cured elastomer region of a torsion repeated rotary wing motion fatigue test sample. The white interior region with the encompassing black exterior region was made with centered concentric uncured elastomers such as shown in FIG. 3. FIG. 7 illustrates a torsion repeated rotary wing motion fatigue test sample with an exterior black elastomer region encompassing an interior red brown elastomer region, with brown crumbs expelled from the interior. FIG. 8 illustrates a torsion repeated rotary wing motion fatigue test sample with an exterior white elastomer region encompassing an interior black elastomer region, with black crumbs expelled from the interior. FIG. 9 illustrates mold bonding nonelastomeric shim members and elastomeric shim member layers together to provide an alternating laminated bearing stack with said exterior elastomer region exterior of said interior elastomer region with a mold with a transfer elasomer spue proximate the interior center region with the transferred elastomer visually common with the nontransferred interior elastomer regions shim layers which are layed up between the nonelastomeric shim member layers. FIG. 10 illustrates mold bonding nonelastomeric shim members and elastomeric shim member layers together to provide an alternating laminated bearing stack with said exterior elastomer region exterior of said interior elastomer region with a mold with a transfer elasomer spue proximate the exterior perimeter region with the transferred elastomer visually common with the nontransferred exterior elastomer regions shim layers which are layed up between the nonelastomeric shim member layers. The different optical characteristic elastomer is strategically placed in a predetermined bearing stack location to provide a damage detection indicator, with the different optical characteristic elastomer visible when a damage elastomer void propagates from the exterior surface to a depth of damage importance. FIG. 11 illustrates a two color elastomer marker band placed in a predetermined layer of a rotary wing spherical bearing.

In an embodiment the invention includes a rotary wing aircraft bearing 20 to provide a constrained relative motion between a first rotary wing aircraft member 22 and a second rotary wing aircraft member 24, the bearing 20 including an elastomeric mold bonded laminated bearing stack 26, the elastomeric mold bonded laminated bearing stack 26 including a plurality of mold bonded alternating layers of nonelastomeric shim member layers 28 and elastomeric shim members layers 30, the alternating layers having an exterior surface 32 and an interior center 34 distal from the exterior surface 32. At least one of the elastomeric shim members layers 30 includes an interior elastomer region 36 distal from the exterior surface 32, the interior elastomer region 36 comprised of an interior cured elastomer composition 38 having at least a first interior optical characteristic ingredient. The at least one elastomeric shim members layer 30 includes an exterior elastomer region 40 encompassing the interior elastomer region 36, the exterior elastomer region 40 proximate the exterior surface 32, the exterior elastomer region 40 comprised of an exterior cured elastomer composition 42 having at least a second exterior optical characteristic ingredient, the at least second exterior optical characteristic ingredient different than the interior cured elastomer composition first interior optical characteristic ingredient, wherein with an elastomer void crack 44 propogating from the exterior surface 32 inward towards the interior elastomer region 36 and a repeated rotary wing aircraft relative motion between the first rotary wing aircraft member 22 and the second rotary wing aircraft member 24 generates a plurality of interior cured elastomer composition crumbs 46 to be expelled from the elastomer void 44, the interior cured elastomer composition crumbs 46 optically distinguishable from the exterior cured elastomer composition 42. Preferably a plurality of the elastomeric shim member layers 30 include an interior elastomer region 36 and all of the elastomeric shim member layers exterior elastomer regions 40 are optically distinguishable from the interior elastomer regions 36. Preferably the first interior optical characteristic ingredient is comprised of a dye. Preferably the dye is not soluble in the interior cured elastomer. Preferably the dye is water soluble. Preferably the dye is fluorescent. Preferably the first interior optical characteristic ingredient is comprised of a carbon black substitute. Preferably the carbon black substitute is comprised of silica. Preferably the ingredients further include a nonblack colorant. In an embodiment the interior elastomer region 36 is black and preferably the first interior optical characteristic ingredient is comprised of carbon black. Preferably the exterior elastomer region and the exterior surface are black and the second exterior optical characteristic ingredient is comprised of carbon black. In an embodiment the second exterior optical characteristic ingredient is comprised of a carbon black substitute. Preferably the exterior elastomer region 40 extends inward towards the interior elastomer region 36 with a predetermined exterior elastomer region radial dimension d. Preferably the predetermined exterior elastomer region radial dimension d is in the range from 1% of r to 50% of r with r being the predetermined radial dimension of the elastomeric shim member layer 30, preferably with 2% r≤d≤30% r. Preferably the at least one elastomeric shim member 30 has the predetermined elastomeric shim layer radial dimension r greater than a predetermined exterior elastomer region radial dimension d with d in the range from 0.01 r to 0.5r, preferably with 0.02r≤d≤0.3r. Preferably the interior elastomer region 36 is centered about a bearing center axis 48 with the interior elastomer region extending outward from the bearing center axis with a predetermined interior elastomer region dimension. Preferably the interior elastomer region predetermined interior elastomer region dimension is r-d. Preferably with hollow elastomer bearing center axis bearings that have a hollow nonelastomer void proximate the center axis 48 the predetermined elastomeric shim layer radial dimension r is from the centerline of the elastomer layer section. Preferably with hollow elastomer bearing center axis bearings the bearing has an inboard exterior surface 32 proximate the center axis 48 and an outboard exterior surface 32 distal from the axis 48. Preferably the at least one elastomeric shim member layer 30 with the interior elastomer region interior cured elastomer composition 38 and the exterior elastomer region exterior cured elastomer composition 42 are disposed at a predetermine degradation position 50 within the laminated bearing stack 26. Preferably the at least one elastomeric shim member layer 30 at the predetermine degradation position 50 within the laminated bearing stack 26 is visible by an observing inspector when installed in the rotary wing aircraft 52, preferably installed in a bearing location 54 in a rotary wing system 53 for bearing a compressive load between the first member 22 and the second member 24 in a first direction 56 and the repeated relative motion comprises an alternating shear load in a first and second shearing direction 58 with the compressive load first direction 56 nonparallel to the first and second shearing direction 58, and preferably substantially perpendicular and normal to the first and second shearing direction 58. Preferably the at least one elastomeric shim member layer 30 with the interior elastomer region interior cured elastomer composition 38 and the exterior elastomer region exterior cured elastomer composition 42 are disposed at a predetermine degradation position 50 within the laminated bearing stack and includes a third elastomer region cured elastomer composition 38' having a third optical characteristic different from the interior elastomer region interior cured elastomer composition 38 and the exterior elastomer region exterior cured elastomer composition 42. Preferably the at least first interior optical characteristic ingredient is comprised of a carbon black substitute and a a nonblack colorant, and the second exterior optical characteristic ingredient is comprised of carbon black. Preferably the carbon black substitute is comprised of silica and the nonblack colorant is a yellow pigment. Preferably the interior elastomer region 36 is yellow and the exterior elastomer region 40 is black. Preferably the at least one elastomeric shim layer 30 is visible by an observing inspector when installed in a bearing location 54 for bearing a compressive load between the first member and the second member in a first direction 56 and the repeated relative motion comprises an alternating shear load in a first and second shearing direction 58 with the compressive load first direction 56 nonparallel and normal to to the first and second shearing direction 58. Preferably the at least one elastomeric shim layer 30 has an elastomer layer thickness t (thickness t in the bearing compressive load first direction 56 between the nonelastomeric members) and an exterior surface bulge area BA, with the elastomeric shim layer 30 having a bonded elastomer interface load area LA (bond interface between elastomer and nonelastomer that elastomer is bonded to), with the elastomeric shim layer 30 having a shape factor SF with 0.1<SF<60, preferably with SF=LA/BA and 0.25≤SF≤50. Preferably the preferred range for the interior elastomer region 36 bonded interface load area compared to the total LA is between 25% to 98% of the total LA, prefer 50% to 96% of the total LA. Preferably the at least one elastomeric shim layer 30 with the interior elastomer region interior cured elastomer composition 38 and the exterior elastomer region exterior cured elastomer composition 42 are disposed at a predetermine degradation position 50 within the bearing stack 26 and the exterior elastomer region 40 extends inward towards the interior elastomer region 36 with a predetermined exterior elastomer region radial dimension d, preferably with d in the range from 1% of r to 50% of r, prefer 2% r≤d≤30% r.

In an embodiment the invention includes a method of making a rotary wing aircraft bearing 20 to provide a constrained relative motion between a first rotary wing aircraft member 22 and a second rotary wing aircraft member 24. The method includes providing a plurality of nonelastomeric shim members 28 and providing a plurality of elastomeric shim member layers 30, at least one of the elastomeric shim member layers 30 comprised of an interior elastomer region 36, the interior elastomer region 36 comprised of an interior elastomer composition 38 having at least a first interior optical characteristic ingredient, and an exterior elastomer region 40, the exterior elastomer region comprised of an exterior elastomer composition 42 having at least a second exterior optical characteristic ingredient, the at least second exterior optical characteristic ingredient different than the interior elastomer composition first interior optical characteristic ingredient, the exterior elastomer region 40 disposed exterior from the interior elastomer region 36. The method includes bonding the nonelastomeric shim members 28 and the elastomeric shim member layers 30 together to provide an alternating laminated bearing stack 26 with the exterior elastomer region 40 exterior of the interior elastomer region 36, the exterior elastomer region 40 proximate an exterior surface 32 of the alternating laminated bearing stack 26, the exterior elastomer region 40 comprised of an exterior cured elastomer composition 42, the at least second exterior optical characteristic ingredient different than the interior cured elastomer composition first interior optical characteristic ingredient, wherein with an elastomer void crack 44 propagating from the exterior surface 32 inward towards the interior elastomer region 36 and a repeated rotary wing aircraft relative motion between the first rotary wing aircraft member and the second rotary wing aircraft member generates a plurality of interior cured elastomer composition crumbs 46 to be expelled from the elastomer void 44, the interior cured elastomer composition crumbs 46 optically distinguishable from the exterior cured elastomer composition 42. Preferably the method includes installing the rotary wing aircraft bearing 20 in a rotary wing aircraft 52 with an observable portion of the exterior elastomer region 40 visible to an inspector wherein the optically distinguishable interior cured elastomer composition crumbs 46 are detected by the inspector. Preferably a plurality of the elastomeric shim member layers 30 include an interior elastomer region 36 and all of the elastomeric shim member layers exterior elastomer regions 40 are optically distinguishable from the interior elastomer regions 36. Preferably the first interior optical characteristic ingredient is comprised of a dye. Preferably the dye is not soluble in the interior elastomer. Preferably the dye is water soluble, preferably with the dye fluorescent. Preferably the first interior optical characteristic ingredient is comprised of a carbon black substitute. Preferably the carbon black substitute is comprised of silica. Preferably the ingredients further include a nonblack colorant. In an embodiment the first interior optical characteristic ingredient is comprised of carbon black, with the second exterior optical characteristic ingredient is comprised of a carbon black substitute. Preferably the second exterior optical characteristic ingredient is comprised of carbon black. Preferably the exterior elastomer region 40 extends inward towards the interior elastomer region 36 with a predetermined exterior elastomer region radial dimension d, preferably with d in the range from 1% of r to 50% of r, preferably 2% r≤d≤30% r. Preferably the at least one elastomeric shim member 30 has a predetermined elastomeric shim layer radial dimension r greater than the predetermined exterior elastomer region radial dimension d with d in the range from 0.01r to 0.5r preferably 0.02r≤d≤0.3r. Preferably the interior elastomer region 36 is centered about a bearing center axis 48, with the interior elastomer region 36 extending outward from the bearing center axis with a predetermined interior elastomer region dimension (preferably r-d). Preferably with hollow elastomer bearing bearings with a void proximate the center axis the predetermined elastomeric shim layer radial dimension r is from the centerline of the elastomer layer. Preferably the at least one elastomeric shim member layer 30 with the interior elastomer region interior cured elastomer composition 38 and the exterior elastomer region exterior cured elastomer composition 42 are disposed at a predetermine degradation position 50 within the laminated bearing stack 26. Preferably the at least one elastomeric shim member layer 30 at the predetermine degradation position 50 within the laminated bearing stack 26 is visible by an observing inspector when installed in a rotary wing aircraft 52. Preferably the bearing 20 is installed in a bearing location 54 for bearing a compressive load between the first member and the second member in a first direction 56 and the repeated relative motion comprises an alternating shear load in a first and second shearing direction 58 with the compressive load first direction 56 nonparallel to the first and second shearing direction 58. Preferably the at least one elastomeric shim member layer 30 includes a third elastomer region cured elastomer composition 38' having a third optical characteristic different from the interior elastomer region interior cured elastomer composition 38 and the exterior elastomer region exterior cured elastomer composition 42. Preferably the nonelastomeric shim members 28 and the elastomeric shim member layers 30 are bonded together in a mold 60 with the elastomeric shim member layers 30 cured. Preferably the mold 60 includes a elastomer transfer sprue 62 for transferring additional elastomer into the mold. Preferably the elastomer transfer sprue 62 is proximate the interior elastomer region 36, and preferably the additional elastomer appears optically similar to the interior elastomer composition. Preferably the elastomer transfer sprue 62 is proximate the exterior elastomer region 40, and preferably the additional elastomer appears optically similar to the exterior elastomer composition. Preferably the at least first interior optical characteristic ingredient is comprised of a carbon black substitute and a nonblack colorant, and the second exterior optical characteristic ingredient is comprised of carbon black. Preferably the carbon black substitute is comprised of silica and the nonblack colorant is a yellow pigment. Preferably the interior elastomer region 36 is yellow and the exterior elastomer region 40 is black. Preferably the at least one elastomeric shim layer 30 is visible by an observing inspector when installed in a bearing location 54 for bearing a compressive load between the first member and the second member in a first direction 56 and the repeated relative motion comprises an alternating shear load in a first and second shearing direction 58 with the compressive load first direction 56 nonparallel to the first and second shearing direction 58. Preferably the at least one elastomeric shim layer 30 has an elastomer layer thickness t (thickness t in the bearing compressive load first direction 56 between the members) and an exterior surface bulge area BA, with the elastomeric shim layer having a bonded elastomer interface load area LA (bond interface between elastomer and nonelastomer that elastomer is bonded to), with the elastomeric shim layer having a shape factor SF with 0.1<SF<60, preferably with SF=LA/BA, and preferably 0.25≤SF≤50. Preferably the interior elastomer region bonded interface load area compared to the total LA is between 25% to 98% of the total LA, preferably 50% to 96% of the total LA. Preferably the at least one elastomeric shim layer 30 with the interior elastomer region interior cured elastomer composition 38 and the exterior elastomer region exterior cured elastomer composition 42 are disposed at a predetermine degradation position 50 within the bearing stack and the exterior elastomer region 40 extends inward towards the interior elastomer region 36 with a predetermined exterior elastomer region radial dimension d, preferably with d in the range from 1% of r to 50% of r, preferably with 2% r≤d≤30% r.

In an embodiment the invention includes a rotary wing aircraft bearing 20 to provide a rotary wing motion between a first rotary wing aircraft member 22 and a second rotary wing aircraft member 24. The bearing 20 includes an elastomeric bonded laminated bearing stack 26, the elastomeric bonded laminated bearing stack including a plurality of bonded alternating layers of nonelastomeric shim member layers 28 and elastomeric shim members layers 30. The bearing 20 includes a predetermined first elastomeric shim members layer 30 comprised of a first elastomer region 36, the first elastomer region 36 comprised of an first cured elastomer composition 38 having at least a first optical characteristic ingredient, and a second elastomer region 40, the second elastomer region 40 proximate an exterior surface 32, the second elastomer region 40 comprised of a second cured elastomer composition 42 having at least a second optical characteristic ingredient, the at least second optical characteristic ingredient different than the first cured elastomer composition first optical characteristic ingredient, wherein a rotary wing motion elastomer void crack 44 propogating from the exterior surface 32 inward towards an interior of the bearing interior elastomer region with the rotary wing motion generates a plurality of first cured elastomer composition crumbs 46 expelled from the elastomer void 44, the first cured elastomer composition crumbs 46 optically distinguishable from the second cured elastomer composition 42. Preferably the predetermined first elastomeric shim layer 30 has a predetermined stack position 50 within the elastomeric bonded laminated bearing stack 26.

In an embodiment the invention includes a bearing 20 to provide a constrained relative motion between a first member and a second member, the bearing 20 including an elastomeric mold bonded bearing stack 26, the elastomeric mold bonded bearing stack 26 including at least a first mold bonded elastomeric shim layer 30, the at least first mold bonded elastomeric shim layer 30 having an exterior surface 32 and an enclosed interior center 34 distal from the exterior surface 32. The elastomeric shim layer 30 includes an enclosed interior elastomer region 36 distal from the exterior surface 32, the interior elastomer region 36 comprised of an interior cured elastomer composition 38 having at least a first interior optical characteristic ingredient. The elastomeric shim layer 30 includes an exterior elastomer region 40 encompassing the interior elastomer region 36, the exterior elastomer region 40 proximate the exterior surface 32, the exterior elastomer region 40 comprised of an exterior cured elastomer composition 42 having at least a second exterior optical characteristic ingredient, the at least second exterior optical characteristic ingredient different than the interior cured elastomer composition first interior optical characteristic ingredient, wherein an elastomer void crack 44 propogating from the exterior surface 32 inward towards the interior elastomer region 36 and a repeated relative motion between the first member and the second member generates a plurality of interior cured elastomer composition crumbs 46 to be expelled from the elastomer void 44, the interior cured elastomer composition crumbs 46 optically distinguishable from the exterior cured elastomer composition 42. Preferably the interior cured elastomer composition crumbs 46 come from and are formed from the interior cured elastomer composition 38, preferably the solid interior cured elastomer of region 36 is broken up into crumbs 46 with the repeated relative motion proximate an interior portion of the propogating crack 44 and expelled outward towards the exterior 32, the interior cured elastomer composition crumbs optically distinguishable from exterior elastomer composition and cured elastomer composition crumbs. Preferably the bearing 20 is installed in a bearing location 54 for bearing a compressive load between the first member and the second member in a first direction 56 and the repeated relative motion comprises an alternating shear load in a first and second shearing direction 58 with the compressive load first direction 56 nonparallel to the first and second shearing direction 58, preferably with the bearing installed the crumbs 46 are visible by an observing inspector. Preferably the expelled interior cured elastomer composition crumbs 46 are persistent in that they preferably collect and stick to the exterior surface 32, preferably remaining when exposed to a fluid stream, such as the bearing 20 moving through air or a water stream/current applied to the bearing. Preferably a plurality of the mold bonded elastomeric shim layers 30 have the interior elastomer region 36 and all of the elastomeric shim layers exterior elastomer regions 40 are optically distinguishable from the interior elastomer regions 36. Preferably the first interior optical characteristic ingredient is comprised of a dye, preferably wherein the dye is not soluble in the interior cured elastomer. Preferably the dye is water soluble, preferably the dye is fluorescent. Preferably the first interior optical characteristic ingredient is comprised of a carbon black substitute, preferably wherein the carbon black substitute is comprised of silica. Preferably the ingredients further include a nonblack colorant. In an embodiment the first interior optical characteristic ingredient is comprised of carbon black, and the second exterior optical characteristic ingredient is comprised of a carbon black substitute. Preferably the second exterior optical characteristic ingredient is comprised of carbon black. Preferably the exterior elastomer region 40 extends inward towards the interior elastomer region 36 with a predetermined exterior elastomer region radial dimension d, preferably with d in the range from 1% of r to 50% of r, preferably 2% r≤d≤30% r. Preferably the first mold bonded elastomeric shim layer 30 has a predetermined elastomeric shim layer radial dimension r greater than predetermined exterior elastomer region radial dimension d with d in the range from 0.01 r to 0.5r, preferably 0.02r≤d≤0.3r. Preferably the interior elastomer region 36 is centered about a bearing center axis 48, with the interior elastomer region 36 extending outward. Preferably with hollow elastomer bearing centers r is at the centerline of the elastomer layer section. Preferably the at least one elastomeric shim layer 30 with the interior elastomer region interior cured elastomer composition 38 and the exterior elastomer region exterior cured elastomer composition 42 are disposed at a predetermine degradation position 50 within the bearing stack 26. Preferably the at least one elastomeric shim layer 30 at the predetermine degradation position 50 within the bearing stack is visible by an observing inspector when installed in a bearing location 54 for bearing a compressive load between the first member and the second member in a first direction 56 and the repeated relative motion comprises an alternating shear load in a first and second shearing direction 58 with the compressive load first direction 56 nonparallel and preferably normal to the first and second shearing direction 58. Preferably the at least one elastomeric shim layer 30 with the interior elastomer region interior cured elastomer composition 38 and the exterior elastomer region exterior cured elastomer composition 42 are disposed at a predetermine degradation position 50 within the bearing stack 26 and include a third elastomer region cured elastomer composition 38' having a third optical characteristic different from the interior elastomer region interior cured elastomer composition 38 and the exterior elastomer region exterior cured elastomer composition 42. Preferably the at least one elastomeric shim layer 30 within the bearing stack 26 is visible by an observing inspector when installed in a bearing location 54 for bearing a compressive load between the first member and the second member in a first direction 56 and the repeated relative motion comprises an alternating shear load in a first and second shearing direction 58 with the compressive load first direction 56 nonparallel to the first and second shearing direction 58. Preferably the at least one elastomeric shim layer 30 has an elastomer layer thickness t (thickness t in the bearing compressive load first direction 56 between the members) and an exterior surface bulge area BA, with the elastomeric shim layer having a bonded elastomer interface load area LA (bond interface between elastomer and nonelastomer that elastomer is bonded to) with the elastomeric shim layer 30 having a shape factor SF with 0.1<SF<60. Preferably with layer 30 SF=LA/BA, preferably with 0.25≤SF≤50. Preferably with layer 30 the preferred range for the interior elastomer region bonded interface load area compared to the total LA is between 25% to 98% of the total LA, preferably 50% to 96% of the total LA. Preferably the at least one elastomeric shim layer 30 with the interior elastomer region interior cured elastomer composition 38 and the exterior elastomer region exterior cured elastomer composition 42 are disposed at a predetermine degradation position within the bearing stack and the exterior elastomer region extends inward towards the interior elastomer region with a predetermined exterior elastomer region radial dimension d, preferably with d in the range from 1% of r to 50% of r, preferably 2% r≤d≤30% r. Preferably the at least first interior optical characteristic ingredient is comprised of a carbon black substitute and a nonblack colorant, and the second exterior optical characteristic ingredient is comprised of carbon black. Preferably the carbon black substitute is comprised of silica and the nonblack colorant is a yellow pigment. Preferably the interior elastomer region is yellow and the exterior elastomer region is black. Preferably the bearing is a rotary wing aircraft bearing for a rotary wing aircraft, with the bearing installed in a rotary wing system of a rotary wing aircraft.

In an embodiment the invention includes a method of making a bearing 20 to provide a constrained relative motion between a first member and a second member, the method includes providing at least a first nonelastomeric member surface 28' and at least a second nonelastomeric member surface 28". The method includes providing at least a first elastomeric shim layer 30 between the first nonelastomeric member surface 28' and the at least second nonelastomeric member surface 28" in a mold 60, and bonding the first elastomeric shim layer 30 to the first nonelastomeric member surface 28' and the second nonelastomeric member surface 28" in the mold 60 to provide an elastomeric mold bonded bearing stack 26, with first mold bonded elastomeric shim layer 30 having an exterior surface 32 and an interior center 34 distal from the exterior surface 32, the elastomeric shim layer 30 comprised of an enclosed interior bonded elastomer region 36 distal from the exterior surface 32, the interior elastomer region 36 comprised of an interior cured elastomer composition 38 having at least a first interior optical characteristic ingredient, and the elastomeric shim layer 30 comprised of an exterior bonded elastomer region 40 encompassing the interior bonded elastomer region 36, the exterior elastomer region 40 proximate the exterior surface 32, the exterior elastomer region 40 comprised of an exterior cured elastomer composition 42 having at least a second exterior optical characteristic ingredient, the at least second exterior optical characteristic ingredient different than the interior cured elastomer composition first interior optical characteristic ingredient, wherein an elastomer void crack 44 propogating from the exterior surface 32 inward towards the interior elastomer region 36 and a repeated relative motion between the first member and the second member generates a plurality of interior cured elastomer composition crumbs 46 to be expelled from the elastomer void 44, the interior cured elastomer composition crumbs 46 optically distinguishable from the exterior cured elastomer composition 42. Preferably the interior cured elastomer composition crumbs 46 are formed from pieces of the interior cured elastomer composition 38 that migrate to the surface, preferably the solid interior cured elastomer 38 is broken up into crumbs with the repeated relative motion proximate an interior portion of the propogating crack 44 and expelled outward towards the exterior 32, with the interior cured elastomer composition crumbs 46 optically distinguishable from the exterior cured elastomer composition crumbs. Preferably the bearing 20 is installed in a bearing location 54 for bearing a compressive load between the first member and the second member in a first direction 56 and the repeated relative motion comprises an alternating shear load in a first and second shearing direction 58 with the compressive load first direction 56 nonparallel and substantially perpendicular to the first and second shearing direction 58. Preferably when installed the crumbs 46 are visible to an observing inspector. Preferably the expelled interior cured elastomer composition crumbs 46 are persistent in that they preferably collect and stick to the exterior surface 32, preferably remaining when exposed to a fluid stream, such as the bearing 20 moving through air or a water stream/current applied to the bearing. Preferably the method includes providing a plurality elastomeric shim layers 30 with the interior elastomer region 36, the plurality of elastomeric shim layers 30 with the interior elastomer region 36 laminated between a plurality of nonelastomeric member surfaces 28',28" with the plurality of elastomeric shim layers exterior elastomer regions 40 optically distinguishable from the interior elastomer regions 36. Preferably the first interior optical characteristic ingredient is comprised of a dye, preferably the dye is not soluble in the interior cured elastomer, preferably wherein the dye is water soluble. Preferably the dye is fluorescent. Preferably the first interior optical characteristic ingredient is comprised of a carbon black substitute, preferably with the carbon black substitute comprised of silica. Preferably the ingredients further include a nonblack colorant. In an embodiment the first interior optical characteristic ingredient is comprised of carbon black, preferably with the second exterior optical characteristic ingredient is comprised of a carbon black substitute. Preferably the second exterior optical characteristic ingredient is comprised of carbon black. Preferably the exterior elastomer region 40 extends inward towards the interior elastomer region 36 with a predetermined exterior elastomer region radial dimension d, preferably with d in the range from 1% of r to 50% of r, preferably with 2% r≤d≤30% r. Preferably the first mold bonded elastomeric shim layer has a predetermined elastomeric shim layer radial dimension r greater than a predetermined exterior elastomer region radial dimension d with d in the range from 0.01r to 0.5r, preferably with 0.02r≤d≤0.3r. Preferably the interior elastomer region is centered about a bearing center axis 48, with the interior elastomer region extending outward away from the bearing center axis with a predetermined interior elastomer region dimension, preferably r-d. Preferably with hollow elastomer bearings 20 with an elastomer hollow void at the center axis 48, the predetermined elastomeric shim layer radial dimension r is from the centerline of the elastomer layer section. Preferably the at least one elastomeric shim layer 30 with the interior elastomer region interior cured elastomer composition 38 and the exterior elastomer region exterior cured elastomer composition 42 are disposed at a predetermine degradation position 50 within the bearing stack 26. Preferably the at least one elastomeric shim layer 30 at the predetermine degradation position 50 within the bearing stack is visible by an observing inspector when installed in a bearing location 54 for bearing a compressive load between the first member and the second member in a first direction 56 and the repeated relative motion comprises an alternating shear load in a first and second shearing direction 58 with the compressive load first direction 56 nonparallel to the first and second shearing direction 58. Preferably the at least one elastomeric shim layer 30 with the interior elastomer region interior cured elastomer composition 38 and the exterior elastomer region exterior cured elastomer composition 42 are disposed at a predetermine degradation position 50 within the bearing stack and include a third elastomer region cured elastomer composition 38' having a third optical characteristic different from the interior elastomer region interior cured elastomer composition 38 and the exterior elastomer region exterior cured elastomer composition 42. Preferably the at least one elastomeric shim layer 30 within the bearing stack is visible by an observing inspector when installed in a bearing location 50 for bearing a compressive load between the first member and the second member in a first direction and the repeated relative motion comprises an alternating shear load in a first and second shearing direction with the compressive load first direction nonparallel to the first and second shearing direction. Preferably the at least one elastomeric shim layer 30 has an elastomer layer thickness t (thickness t in the bearing compressive load first direction 56 between the members) and an exterior surface bulge area BA, with the elastomeric shim layer having a bonded elastomer interface load area LA (bond interface between elastomer and nonelastomer surface area 28', 28" that the elastomer is bonded to), with the elastomeric shim layer having a shape factor SF with $0.1<SF<60$. Preferably SF=LA/BA, preferably with $25 \leq SF \leq 50$. Preferably the interior elastomer region bonded interface load area compared to the total LA is between 25% to 98% of the total LA, preferably 50% to 96% of the total LA. Preferably the at least one elastomeric shim layer 30 with the interior elastomer region interior cured elastomer composition 38 and the exterior elastomer region exterior cured elastomer composition 42 are disposed at a predetermine degradation position 50 within the bearing stack and the exterior elastomer region 40 extends inward towards the interior elastomer region 36 with a predetermined exterior elastomer region radial dimension d, preferably with d in the range from 1% of r to 50% of r, preferably with $2\% r \leq d \leq 30\% r$. Preferably the at least first interior optical characteristic ingredient is comprised of a carbon black substitute and a nonblack colorant, and the second exterior optical characteristic ingredient is comprised of carbon black, preferably with the carbon black substitute comprised of silica and the nonblack colorant is a yellow pigment. Preferably the interior elastomer region is yellow and the exterior elastomer region is black. Preferably the bearing is a rotary wing aircraft bearing for a rotary wing aircraft, with the bearing installed in a rotary wing system of a rotary wing aircraft.

Preferably the interior elastomer composition 38 is a fully functioning elastomer constituent of the bearing assembly. Preferably the interior elastomer composition 38 is in the path where damage propagates through the bearing assembly part. Preferably the interior elastomer region 36 is a colored elastomer in a working section of the elastomer rubber which is not visible when the part is new and removed from the mold and is in the degradation path where after installation and from in-service use conditions is predetermined that degradation elastomer void crack growth should occur and is at a depth from the exterior surface which is calibrated to the bearing part's replacement criteria. Preferably the expelled interior crumbs 46 provide a persistent visual indicator of when to replace a elastomer rubber bearing part so that the observing inspector operator does not need to be in sight of the elastomer rubber bearing part all the time, and preferably does not need to observe the part during repeated relative motions. Preferably the exterior surface 32 and the exterior elastomer region 40 do not wear away during the installed use. Preferably the interior elastomer composition 38 is disposed and cured in place at a predetermined depth below the surface 32 wherein a likely crack initiation site should originate in a predetermined degradation position and the crack propagation into the interior elastomer region 36 brings the colored elastomer material composition 38 to the surface 32.

Figure 20:
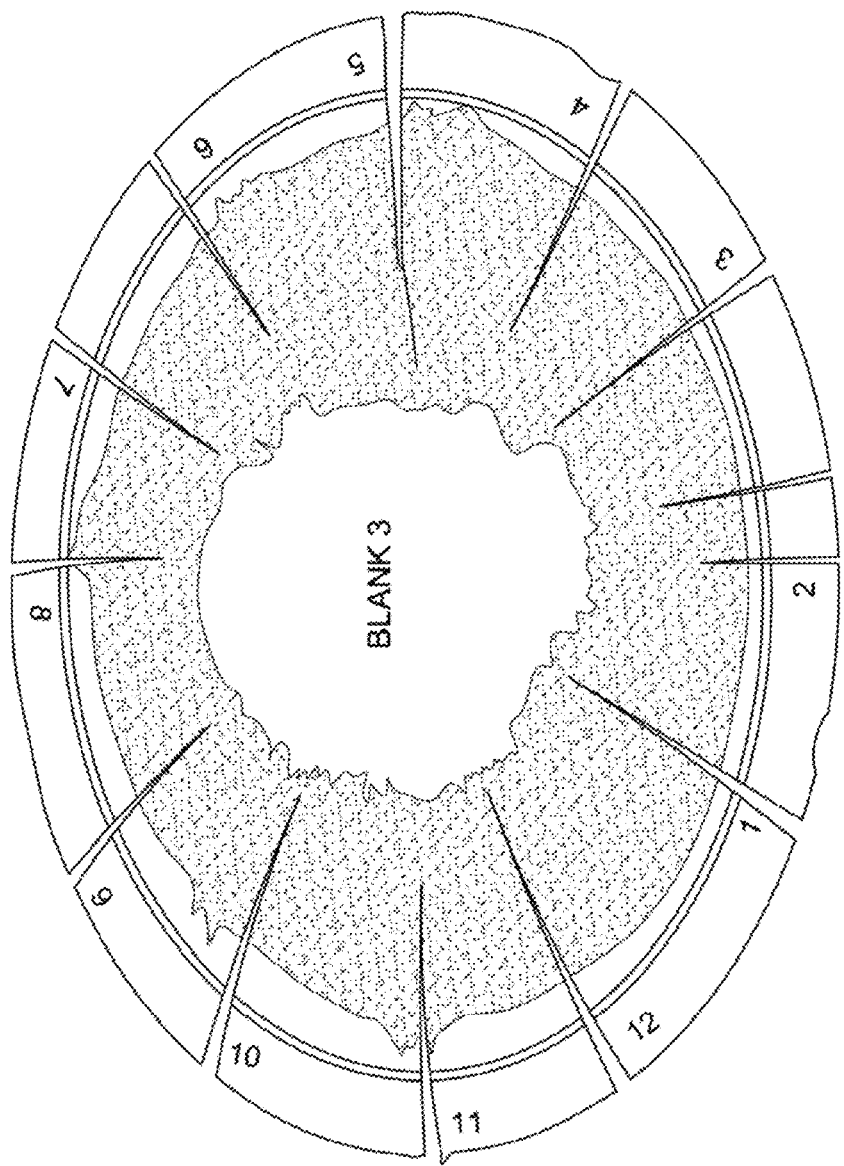
FIG. 20 illustrates a photograph taken of a yellow elastomer composition contrasting with an exterior black elastomer composition.
Figure 21:
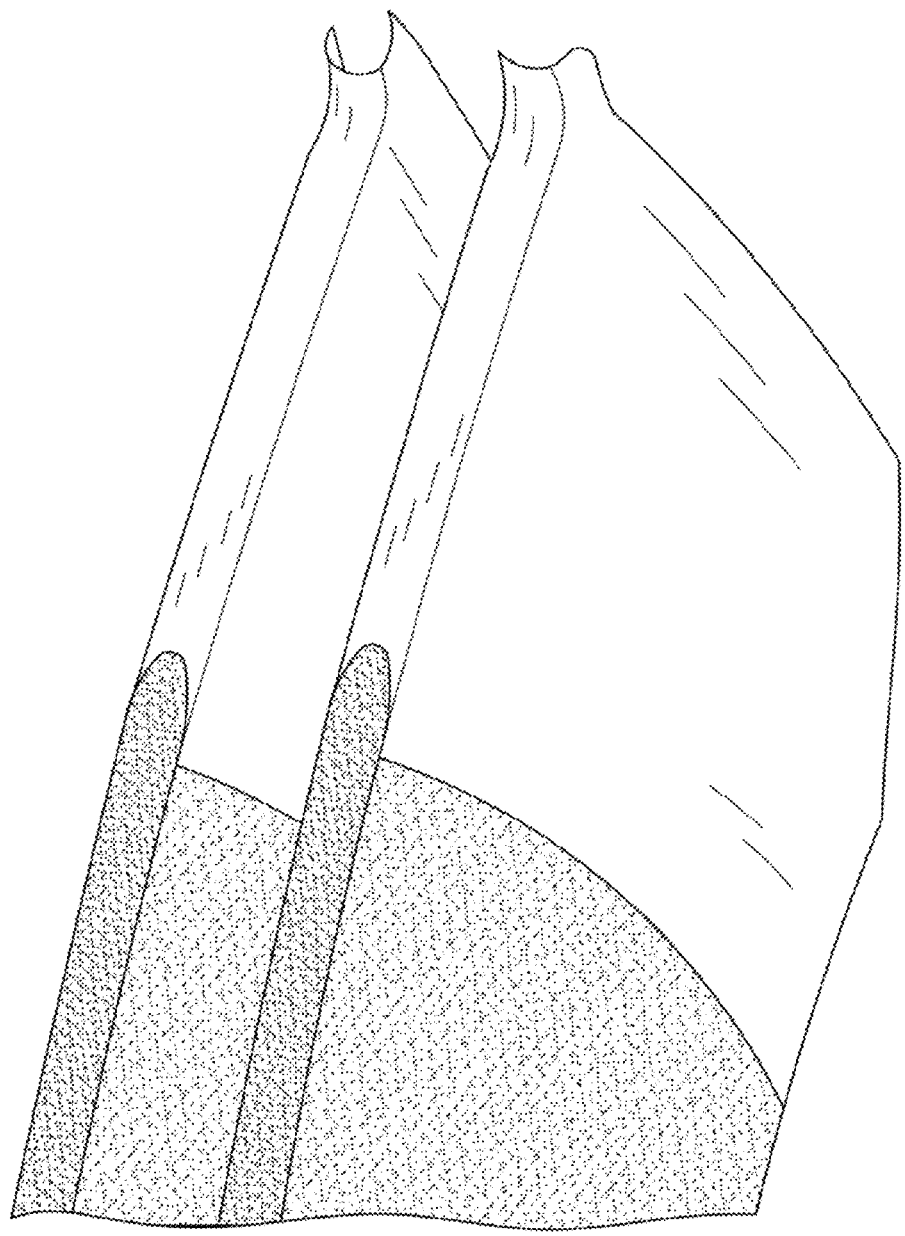
FIG. 21 illustrates a photograph taken of two elastomer shim layers edge views showing the high contrast between the yellow elastomer composition and the exterior black elastomer composition.

Preferably the contrasting particle interior crumbs 46 are expelled outward to the surface 32 with such migrating from the crack propagation front of crack 44. A preferred embodiment includes yellow contrasting material elastomer composition 38 with a host black material elastomer composition 42. Such yellow contrasting elastomer composition 38 with exterior black elastomer composition 42 is shown in FIGS. 20 and 21 with the yellow elastomer showing high contrast and edge view of two layers showing a predetermined uniform d dimension.

Figure 22:
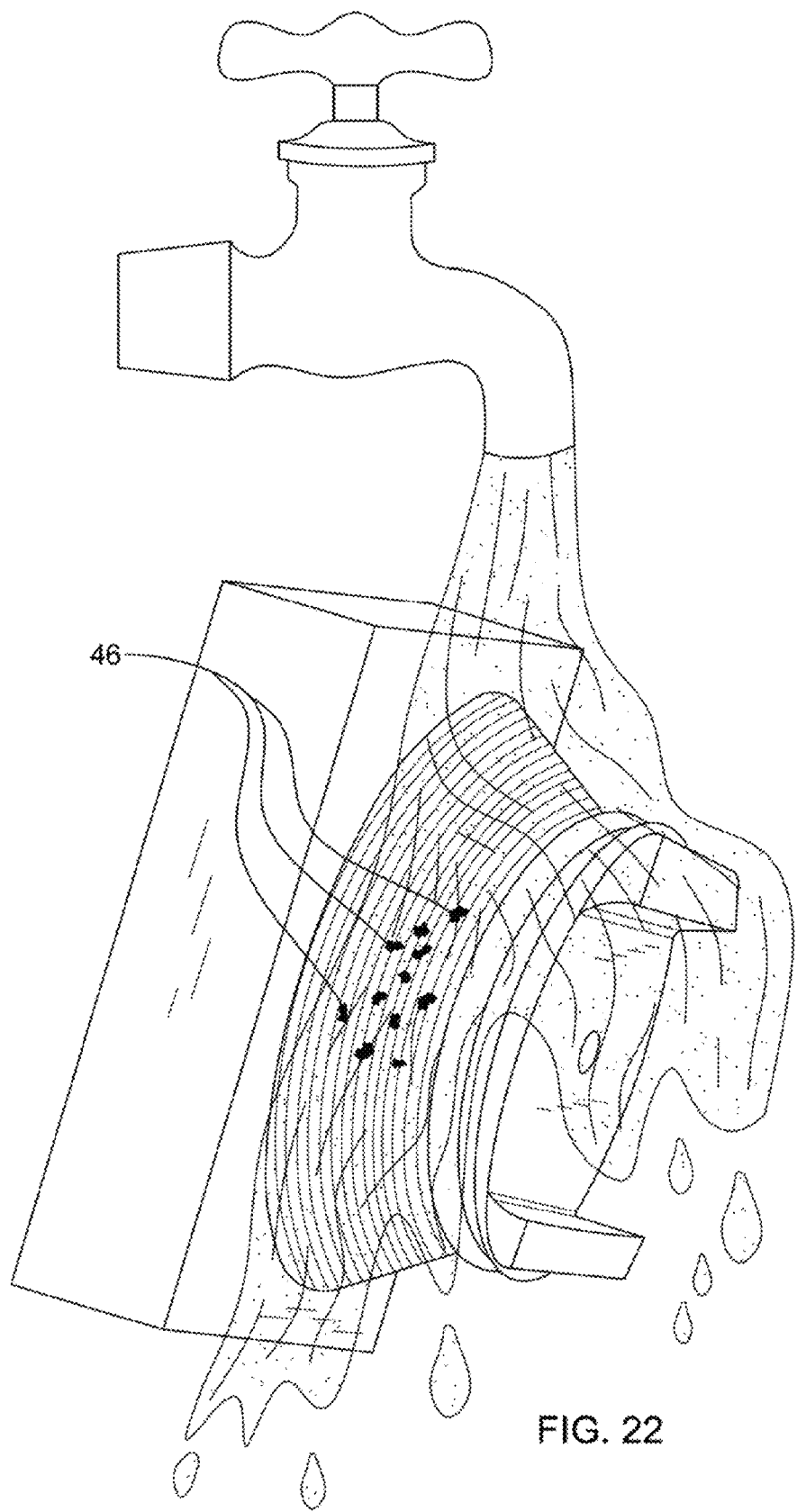
FIG. 22 illustrates a photograph taken showing that yellow rubber particles 46 stay on the bearing part under a forceful stream of water.

Preferably the elastomer particle crumbs 46 are sticky and persist on the surface 32 the bearing part and are therefore providing a persistent indicator. FIG. 22 show that yellow rubber particles 46 stay on the bearing part under a forceful stream of water. Preferably the colored elastomer interior region 36 is in such a predetermined location with a predetermined edge distance dimension wherein the elastomer particle crumbs 46 comes to the surface 32 at a predetermined point of remaining service life of the bearing 20, preferably calibrated by testing of such bearings 20.

It will be apparent to those skilled in the art that various modifications and variations can be made to the invention without departing from the spirit and scope of the invention. Thus, it is intended that the invention cover the modifications and variations of this invention provided they come within the scope of the appended claims and their equivalents. It is intended that the scope of differing terms or phrases in the claims may be fulfilled by the same or different structure(s) or step(s).

The invention claimed is:

1. A rotary wing aircraft bearing to provide a constrained relative motion between a first rotary wing aircraft member and a second rotary wing aircraft member, said bearing including an elastomeric mold bonded laminated bearing stack, said elastomeric mold bonded laminated bearing stack including a plurality of mold bonded alternating layers of nonelastomeric shim member layers and elastomeric shim member layers, said alternating layers having an exterior surface and an interior center distal from said exterior surface, at least one of said elastomeric shim member layers comprised of an interior elastomer region distal from said exterior surface, said interior elastomer region comprised of an interior cured elastomer composition having at least a first interior optical characteristic ingredient, and an exterior elastomer region encompassing said interior elastomer region, said exterior elastomer region proximate said exterior surface, said exterior elastomer region comprised of an exterior cured elastomer composition having at least a second exterior optical characteristic ingredient, said at least a second exterior optical characteristic ingredient different than said interior cured elastomer composition first interior optical characteristic ingredient, wherein with an elastomer void crack propagating from said exterior surface inward towards said interior elastomer region and a repeated rotary wing aircraft relative motion between said first rotary wing aircraft member and said second rotary wing aircraft member generates a plurality of interior cured elastomer composition crumbs to be expelled from said elastomer void, said interior cured elastomer composition crumbs optically distinguishable from said exterior cured elastomer composition.

2. The rotary wing aircraft bearing as claimed in claim 1 wherein a plurality of said elastomeric shim member layers include an interior elastomer region and all of said elastomeric shim member layers exterior elastomer regions are optically distinguishable from said interior elastomer regions.

3. The rotary wing aircraft bearing as claimed in claim 1 wherein said first interior optical characteristic ingredient is comprised of a dye.

4. The rotary wing aircraft bearing as claimed in claim 3 wherein said dye is not soluble in said interior cured elastomer composition.

5. The rotary wing aircraft bearing as claimed in claim 4 wherein said dye is water soluble and fluorescent.

6. The rotary wing aircraft bearing as claimed in claim 1 wherein said first interior optical characteristic ingredient is comprised of a carbon black substitute.

7. The rotary wing aircraft bearing as claimed in claim 6 wherein said carbon black substitute is comprised of silica.

8. The rotary wing bearing as claimed in claim 7 wherein said ingredients further include a nonblack colorant.

9. The rotary wing aircraft bearing as claimed in claim 1 wherein said first interior optical characteristic ingredient is comprised of carbon black.

10. The rotary wing aircraft bearing as claimed in claim 1 wherein said second exterior optical characteristic ingredient is comprised of carbon black.

11. The rotary wing aircraft bearing as claimed in claim 1 wherein said second exterior optical characteristic ingredient is comprised of a carbon black substitute.

12. The rotary wing aircraft bearing as claimed in claim 1 wherein said exterior elastomer region extends inward towards said interior elastomer region with a predetermined exterior elastomer region radial dimension.

13. The rotary wing aircraft bearing as claimed in claim 1 wherein said at least one elastomeric shim member layer has a predetermined elastomeric shim layer radial dimension (r) greater than a predetermined exterior elastomer region radial dimension (d) with (d) in the range from 0.01(r) to 0.5(r).

14. The rotary wing aircraft bearing as claimed in claim 1 wherein said interior elastomer region is centered about a bearing center axis, with said interior elastomer region extending outward from said bearing center axis with a predetermined interior elastomer region dimension.

15. The rotary wing aircraft bearing as claimed in claim 1 wherein said at least one elastomeric shim member layer with said interior elastomer region interior cured elastomer composition and said exterior elastomer region exterior cured elastomer composition are disposed at a predetermined degradation position within said laminated bearing stack.

16. The rotary wing aircraft bearing as claimed in claim 15 wherein said at least one elastomeric shim member layer at said predetermined degradation position within said laminated bearing stack is visible by an observing inspector when installed in said rotary wing aircraft.

17. The rotary wing aircraft bearing as claimed in claim 15 wherein said at least one elastomeric shim member layer with said interior elastomer region interior cured elastomer composition and said exterior elastomer region exterior cured elastomer composition are disposed at a predetermined degradation position within said laminated bearing stack includes a third elastomer region cured elastomer composition having a third optical characteristic different from said interior elastomer region interior cured elastomer composition and said exterior elastomer region exterior cured elastomer composition.

18. The rotary wing aircraft bearing as claimed in claim 1 wherein said at least first interior optical characteristic ingredient is comprised of a carbon black substitute and a nonblack colorant, and said second exterior optical characteristic ingredient is comprised of carbon black.

19. The rotary wing aircraft bearing as claimed in claim 18 wherein said carbon black substitute is comprised of silica and said nonblack colorant is a yellow pigment.

20. The rotary wing aircraft bearing as claimed in claim 1 wherein said interior elastomer region is yellow and said exterior elastomer region is black.

21. The bearing as claimed in claim 1 wherein said at least one elastomeric shim layer is visible by an observing inspector when installed in a bearing location for bearing a compressive load between said first member and said second member in a first direction and said repeated relative motion comprises an alternating shear load in a first and second shearing direction with said compressive load first direction nonparallel to said first and second shearing direction.

22. The bearing as claimed in claim 1 wherein said at least one elastomeric shim member layer has an elastomer layer thickness (t) and an exterior surface bulge area (BA), with said elastomeric shim member layer having a bonded elastomer interface load area (LA), with said elastomeric shim member layer having a shape factor (SF) with 0.1<(SF)<60.

23. The bearing as claimed in claim 1 wherein said at least one elastomeric shim member layer with said interior elastomer region interior cured elastomer composition and said exterior elastomer region exterior cured elastomer composition are disposed at a predetermine degradation position within said bearing stack and said exterior elastomer region extends inward towards said interior elastomer region with a predetermined exterior elastomer region radial dimension.

24. A rotary wing aircraft bearing to provide a rotary wing motion between a first rotary wing aircraft member and a second rotary wing aircraft member, said bearing including an elastomeric bonded laminated bearing stack, said elastomeric bonded laminated bearing stack including a plurality of bonded alternating layers of a nonelastomeric shim member layer and an elastomeric shim member layer, a predetermined first elastomeric shim member layer comprised of a first elastomer region, said first elastomer region comprised of an first cured elastomer composition having at least a first optical characteristic ingredient, and a second elastomer region, said second elastomer region proximate an exterior surface, said second elastomer region comprised of a second cured elastomer composition having at least a second optical characteristic ingredient, said at least second optical characteristic ingredient different than said first cured elastomer composition first optical characteristic ingredient, wherein a rotary wing motion elastomer void crack propagating from said exterior surface inward towards an interior of a bearing interior elastomer region with said rotary wing motion generates a plurality of first cured elastomer composition crumbs expelled from said elastomer void crack, said first cured elastomer composition crumbs optically distinguishable from said second cured elastomer composition.

25. The bearing as claimed in claim 24 wherein predetermined first elastomeric shim member layer has a predetermined stack position within said elastomeric bonded laminated bearing stack.

26. A bearing to provide a constrained relative motion between a first member and a second member, said bearing including
- an elastomeric mold bonded bearing stack, said elastomeric mold bonded bearing stack including at least a first mold bonded elastomeric shim layer, said at least first mold bonded elastomeric shim layer having an exterior surface and an interior center distal from said exterior surface,
- said first mold bonded elastomeric shim layer comprised of an enclosed interior elastomer region distal from said exterior surface, said interior elastomer region comprised of an interior cured elastomer composition having at least a first interior optical characteristic ingredient,
- and said first mold bonded elastomeric shim layer comprised of an exterior elastomer region encompassing said interior elastomer region, said exterior elastomer region proximate said exterior surface, said exterior elastomer region comprised of an exterior cured elastomer composition having at least a second exterior optical characteristic ingredient, said at least second exterior optical characteristic ingredient different than said interior cured elastomer composition first interior optical characteristic ingredient, wherein an elastomer void crack propagating from said exterior surface inward towards said interior elastomer region and a repeated relative motion between said first member and said second member generates a plurality of interior cured elastomer composition crumbs to be expelled from said elastomer void, said interior cured elastomer composition crumbs optically distinguishable from said exterior cured elastomer composition.

27. The bearing as claimed in claim 26 with a plurality of said first mold bonded elastomeric shim layer with said interior elastomer region and all of said exterior elastomer regions are optically distinguishable from said interior elastomer regions.

28. The bearing as claimed in claim 26 wherein said first interior optical characteristic ingredient is comprised of a dye.

29. The bearing as claimed in claim 28 wherein said dye is not soluble in said interior cured elastomer composition.

30. The bearing as claimed in claim 29 wherein said dye is water soluble and fluorescent.

31. The bearing as claimed in claim 26 wherein said first interior optical characteristic ingredient is comprised of a carbon black substitute.

32. The bearing as claimed in claim 31 wherein said carbon black substitute is comprised of silica.

33. The bearing as claimed in claim 32 wherein said ingredients further include a nonblack colorant.

34. The bearing as claimed in claim 26 wherein said first interior optical characteristic ingredient is comprised of carbon black.

35. The bearing as claimed in claim 26 wherein said second exterior optical characteristic ingredient is comprised of carbon black.

36. The bearing as claimed in claim 26 wherein said second exterior optical characteristic ingredient is comprised of a carbon black substitute.

37. The bearing as claimed in claim 26 wherein said exterior elastomer region extends inward towards said interior elastomer region with a predetermined exterior elastomer region radial dimension.

38. The bearing as claimed in claim 26 wherein said first mold bonded elastomeric shim layer has a predetermined elastomeric shim layer radial dimension (r) greater than a predetermined exterior elastomer region radial dimension (d) with (d) in the range from 0.01(r) to 0.5(r).

39. The bearing as claimed in claim 26 wherein said interior elastomer region is centered about a bearing center axis, with said interior elastomer region extending outward from said bearing center axis with a predetermined interior elastomer region dimension.

40. The bearing as claimed in claim 26 wherein said at least one first mold bonded elastomeric shim layer with said interior elastomer region interior cured elastomer composition and said exterior elastomer region exterior cured elastomer composition are disposed at a predetermine degradation position within said bearing stack.

41. The bearing as claimed in claim 40 wherein said at least one first mold bonded elastomeric shim layer at said predetermine degradation position within said bearing stack is visible by an observing inspector when installed in a bearing location for bearing a compressive load between said first member and said second member in a first direction and said repeated relative motion comprises an alternating shear load in a first and second shearing direction with said compressive load first direction nonparallel to said first and second shearing direction.

42. The bearing as claimed in claim 40 wherein said at least one first mold bonded elastomeric shim layer with said interior elastomer region interior cured elastomer composition and said exterior elastomer region exterior cured elastomer composition are disposed at a predetermine degradation position within said bearing stack and include a third elastomer region cured elastomer composition having a third optical characteristic different from said interior elastomer region interior cured elastomer composition and said exterior elastomer region exterior cured elastomer composition.

43. The bearing as claimed in claim 26 wherein said at least one first mold bonded elastomeric shim layer within said bearing stack is visible by an observing inspector when installed in a bearing location for bearing a compressive load between said first member and said second member in a first direction and said repeated relative motion comprises an alternating shear load in a first and second shearing direction with said compressive load first direction nonparallel to said first and second shearing direction.

44. The bearing as claimed in claim 26 wherein said at least one first mold bonded elastomeric shim layer has an elastomer layer thickness (t) and an exterior surface bulge area (BA), with said elastomeric shim layer having a bonded elastomer interface load area (LA), with said elastomeric shim layer having a shape factor (SF) with $1<(SF)<60$.

45. The bearing as claimed in claim 26 wherein said at least one mold bonded elastomeric shim layer with said interior elastomer region interior cured elastomer composition and said exterior elastomer region exterior cured elastomer composition are disposed at a predetermine degradation position within said bearing stack and said exterior elastomer region extends inward towards said interior elastomer region with a predetermined exterior elastomer region radial dimension.

46. The bearing as claimed in claim 26 wherein said at least first interior optical characteristic ingredient is comprised of a carbon black substitute and a nonblack colorant, and said second exterior optical characteristic ingredient is comprised of carbon black.

47. The bearing as claimed in claim 46 wherein said carbon black substitute is comprised of silica and said nonblack colorant is a yellow pigment.

48. The bearing as claimed in claim 26 wherein said interior elastomer region is yellow and said exterior elastomer region is black.

\* \* \* \* \*